US011150243B2

(12) United States Patent
Johnson et al.

(10) Patent No.: US 11,150,243 B2
(45) Date of Patent: Oct. 19, 2021

(54) DEVICE FOR RECEIVING AND ANALYSING A SAMPLE WITH DROP-BY-DROP SOLUTION RELEASE FROM A SEALED CAPSULE

(71) Applicant: INTELLIGENT FINGERPRINTING LIMITED, Cambridge (GB)

(72) Inventors: Jonathan Johnson, Cambridge (GB); Mark Hudson, Cambridge (GB)

(73) Assignee: INTELLIGENT FINGERPRINTING LIMITED, Cambridge (GB)

( * ) Notice: Subject to any disclaimer, the term of this patent is extended or adjusted under 35 U.S.C. 154(b) by 523 days.

(21) Appl. No.: 15/553,808

(22) PCT Filed: Feb. 26, 2016

(86) PCT No.: PCT/GB2016/050497
§ 371 (c)(1),
(2) Date: Aug. 25, 2017

(87) PCT Pub. No.: WO2016/135497
PCT Pub. Date: Sep. 1, 2016

(65) Prior Publication Data
US 2018/0031552 A1 Feb. 1, 2018

(30) Foreign Application Priority Data
Feb. 27, 2015 (GB) ..................................... 1503364

(51) Int. Cl.
*G01N 33/558* (2006.01)
*G01N 33/543* (2006.01)
(Continued)

(52) U.S. Cl.
CPC .......... *G01N 33/558* (2013.01); *B01L 3/5023* (2013.01); *G01N 33/54373* (2013.01);
(Continued)

(58) Field of Classification Search
CPC ....... G01N 33/558; G01N 33/543; B01L 3/00
(Continued)

(56) References Cited

U.S. PATENT DOCUMENTS 3,415,361 A * 12/1968 Chambliss .............. B01L 3/508
206/221
3,544,271 A * 12/1970 Nadalin ................. G01N 31/22
436/131
(Continued)

FOREIGN PATENT DOCUMENTS

CN 103857469 A 6/2014
EP 269139 * 6/1988
(Continued)

OTHER PUBLICATIONS

Examination report for Australian Application 2016225217, dated Dec. 23, 2020.*

*Primary Examiner* — Arlen Soderquist
(74) *Attorney, Agent, or Firm* — Lando & Anastasi, LLP

(57) ABSTRACT

A device for receiving and analysing a sample, wherein the analysing involves use of a solution. The device comprises: a sample receiving portion for receiving a sample to be analysed; and a solution capsule having a sealed configuration in which the solution capsule is sealed and a release configuration in which contents of the solution capsule are released via a flow path that provides fluid communication between the solution capsule and the sample receiving portion. The device further comprises a bistable release mechanism comprising an actuator wherein the bistable release mechanism releases only in the event that a force applied to the actuator reaches a threshold force and wherein actuation of the actuator results in one-way conversion of the solution capsule from the sealed configuration into the release configuration.

14 Claims, 16 Drawing Sheets

(51) Int. Cl.
  *B01L 3/00* (2006.01)
  *A61B 5/00* (2006.01)
  *A61B 5/145* (2006.01)
  *A61B 5/1172* (2016.01)

(52) U.S. Cl.
  CPC ......... *A61B 5/1172* (2013.01); *A61B 5/14517* (2013.01); *A61B 5/4266* (2013.01); *A61B 5/4833* (2013.01); *A61B 5/4845* (2013.01); *A61B 5/6826* (2013.01); *B01L 2200/0689* (2013.01); *B01L 2300/0816* (2013.01); *B01L 2400/0406* (2013.01); *B01L 2400/065* (2013.01); *B01L 2400/0683* (2013.01)

(58) Field of Classification Search
  USPC ........................................ 422/82.05; 436/165
  See application file for complete search history.

(56) References Cited

U.S. PATENT DOCUMENTS

| | | | | |
|---|---|---|---|---|
| 3,689,224 A * | 9/1972 | Agnew | B01L 3/502 | 422/413 |
| 3,697,227 A * | 10/1972 | Goldstein | B01L 3/502 | 422/409 |
| 3,713,779 A * | 1/1973 | Sirago | B01L 3/502 | 422/413 |
| 3,740,196 A * | 6/1973 | Stroterhoff | G01N 31/22 | 422/407 |
| 4,261,486 A * | 4/1981 | Bush | B65D 47/0838 | 16/225 |
| 4,336,121 A * | 6/1982 | Enzer | G01N 33/49 | 204/403.02 |
| 4,428,907 A * | 1/1984 | Heijenga | G01N 21/783 | 128/202.22 |
| 4,546,086 A * | 10/1985 | Hounsell | C12M 23/34 | 422/236 |
| 4,604,360 A * | 8/1986 | Hounsell | C12M 45/22 | 422/236 |
| 4,654,127 A * | 3/1987 | Baker | B01L 3/5023 | 204/401 |
| 4,673,657 A * | 6/1987 | Christian | B01J 19/0093 | 422/301 |
| 4,690,801 A * | 9/1987 | Anderson | B01L 3/502 | 356/246 |
| 4,813,432 A * | 3/1989 | Saint-Amand | A61B 10/0096 | 206/363 |
| 4,857,453 A * | 8/1989 | Ullman | G01N 33/54366 | 435/7.92 |
| 4,918,025 A * | 4/1990 | Grenner | B01L 3/5027 | 422/565 |
| 4,943,522 A * | 7/1990 | Eisinger | G01N 33/54386 | 422/537 |
| 4,959,324 A * | 9/1990 | Ramel | B01L 3/5023 | 422/408 |
| 4,965,047 A * | 10/1990 | Hammond | G01N 33/528 | 422/413 |
| 4,981,786 A * | 1/1991 | Dafforn | G01N 33/5302 | 422/412 |
| 5,064,618 A * | 11/1991 | Baker | G01N 33/48707 | 422/82.01 |
| 5,096,669 A * | 3/1992 | Lauks | B01L 3/502707 | 204/403.02 |
| 5,110,552 A * | 5/1992 | Guigan | B01L 3/505 | 356/246 |
| 5,128,104 A * | 7/1992 | Murphy | B01L 3/502 | 206/221 |
| 5,149,505 A * | 9/1992 | English | B01L 3/502 | 422/547 |
| 5,204,063 A * | 4/1993 | Allen | B01L 3/5023 | 422/408 |
| 5,258,314 A * | 11/1993 | Skerratt | B01L 3/505 | 422/416 |
| D342,575 S * | 12/1993 | Ashihara | D24/223 | |
| 5,283,038 A * | 2/1994 | Seymour | A61B 5/411 | 435/287.2 |
| 5,288,463 A * | 2/1994 | Chemelli | B01L 3/502 | 422/417 |
| 5,290,518 A * | 3/1994 | Johnson | B01L 3/502 | 422/413 |
| 5,374,395 A * | 12/1994 | Robinson | G01N 21/253 | 422/562 |
| 5,500,187 A * | 3/1996 | Deoms | B01L 3/502 | 422/417 |
| 5,582,696 A * | 12/1996 | Sheehan | C12Q 1/006 | 204/403.06 |
| 5,652,149 A * | 7/1997 | Mileaf | B01L 3/502 | 422/417 |
| 5,674,653 A * | 10/1997 | Chemelli | B01L 3/505 | 356/246 |
| 5,714,380 A * | 2/1998 | Neri | B01L 3/502 | 422/504 |
| 5,726,010 A * | 3/1998 | Clark | B01L 3/5055 | 435/5 |
| 5,746,975 A * | 5/1998 | Chateau | B01L 3/5025 | 422/415 |
| 5,849,208 A * | 12/1998 | Hayes | B01J 19/0093 | 216/94 |
| 6,017,494 A * | 1/2000 | Ashihara | B01L 3/5023 | 422/412 |
| 6,303,288 B1 * | 10/2001 | Furcht | B01L 3/5027 | 422/504 |
| 6,355,439 B1 * | 3/2002 | Chung | C12N 15/1006 | 428/343 |
| 6,372,431 B1 * | 4/2002 | Cunningham | C12Q 1/6876 | 506/9 |
| 6,436,714 B1 * | 8/2002 | Clawson | B01L 3/5055 | 422/411 |
| 7,090,803 B1 * | 8/2006 | Gould | G01N 33/558 | 422/413 |
| 7,176,034 B2 * | 2/2007 | Efthimiadis | A61B 10/0051 | 422/534 |
| 7,932,099 B2 * | 4/2011 | Egan | B01L 3/5023 | 436/514 |
| 8,066,958 B2 * | 11/2011 | Rasch-Menges | A61B 5/14514 | 15/244.1 |
| 9,724,689 B2 * | 8/2017 | Kisner | G01N 31/22 | |
| 10,035,146 B2 * | 7/2018 | Fuller | A61B 10/0051 | |
| 2001/0026942 A1 * | 10/2001 | Carpenter | A61B 10/0096 | 436/86 |
| 2002/0057991 A1 * | 5/2002 | Kelly | B01L 3/50 | 422/408 |
| 2003/0049848 A1 * | 3/2003 | Gebrian | B01L 99/00 | 436/55 |
| 2003/0180815 A1 * | 9/2003 | Rawson | G01N 33/558 | 435/7.9 |
| 2003/0186456 A1 * | 10/2003 | Stroup | B01F 15/0212 | 436/165 |
| 2004/0005246 A1 * | 1/2004 | Efthimiadis | A61B 10/0051 | 422/534 |
| 2004/0151624 A1 * | 8/2004 | Erdman, Jr. | G01N 31/22 | 422/417 |
| 2004/0214253 A1 * | 10/2004 | Paek | G01N 33/558 | 435/7.92 |
| 2006/0008903 A1 * | 1/2006 | Mussivand | G01N 1/02 | 435/380 |
| 2006/0099719 A1 * | 5/2006 | Curcio | G01N 33/558 | 436/514 |
| 2007/0087357 A1 * | 4/2007 | Clark | G01N 33/54386 | 435/6.11 |
| 2007/0134810 A1 * | 6/2007 | Yang | G01N 33/54366 | 436/514 |
| 2007/0239068 A1 * | 10/2007 | Rasch-Menges | A61B 5/14514 | 600/573 |
| 2008/0145272 A1 * | 6/2008 | Feaster | A61B 5/15105 | 422/400 |
| 2008/0194041 A1 * | 8/2008 | Guirguis | A61B 10/0051 | 436/165 |

(56) References Cited

U.S. PATENT DOCUMENTS

| | | | |
|---|---|---|---|
| 2008/0199851 A1* | 8/2008 | Egan | B01L 3/5029 435/5 |
| 2009/0007969 A1* | 1/2009 | Gundel | F16K 99/0026 137/15.18 |
| 2009/0098559 A1* | 4/2009 | Caragine | A61B 10/0096 435/6.19 |
| 2009/0311739 A1* | 12/2009 | Sestak | C12M 37/06 435/31 |
| 2010/0015658 A1* | 1/2010 | Yang | G01N 33/54366 435/29 |
| 2010/0285490 A1* | 11/2010 | Dees | G01N 33/54373 435/7.1 |
| 2011/0144535 A1 | 6/2011 | Guirguis | |
| 2011/0186466 A1* | 8/2011 | Kurowski | B01L 3/502715 206/524.6 |
| 2012/0058465 A1* | 3/2012 | Mori | G01N 33/54386 435/5 |
| 2012/0149093 A1 | 6/2012 | Gould et al. | |
| 2013/0101184 A1* | 4/2013 | Harrold | A61B 5/150083 382/124 |
| 2013/0280696 A1* | 10/2013 | Millenson | G01N 33/54366 435/5 |
| 2014/0161686 A1* | 6/2014 | Bort | B01L 3/502715 422/502 |
| 2015/0064800 A1* | 3/2015 | Chance | G01N 33/6854 436/501 |
| 2015/0290638 A1* | 10/2015 | Kisner | G01N 31/22 436/164 |
| 2016/0047720 A1* | 2/2016 | Wolgast | G06K 9/00087 506/7 |
| 2016/0121322 A1* | 5/2016 | Fuller | A61B 10/0051 436/501 |

FOREIGN PATENT DOCUMENTS

| | | | |
|---|---|---|---|
| EP | 512390 | * | 11/1992 |
| JP | 8-262023 | * | 10/1996 |
| JP | 2006-170858 | * | 6/2006 |
| JP | 2007064829 | * | 3/2007 |
| JP | 2009531694 A | | 9/2009 |
| JP | 2009532675 A | | 9/2009 |
| JP | 2011089968 | * | 5/2011 |
| JP | 2011089968 A | | 5/2011 |
| JP | 2012063175 A | | 3/2012 |
| WO | 9918436 A1 | | 4/1999 |
| WO | 2005045408 A1 | | 5/2005 |
| WO | 2006119203 A2 | | 11/2006 |
| WO | 2006137785 A1 | | 12/2006 |
| WO | 2007026814 A1 | | 3/2007 |
| WO | 2010132453 A2 | | 11/2010 |
| WO | 2012170435 A2 | | 12/2012 |

* cited by examiner

2

DEVICE FOR RECEIVING AND ANALYSING A SAMPLE WITH DROP-BY-DROP SOLUTION RELEASE FROM A SEALED CAPSULE

CROSS-REFERENCE TO RELATED APPLICATIONS

This application is a U.S. national phase application under 35 U.S.C. § 371 of International Patent Application Serial No. PCT/GB2016/050497, titled "A DEVICE FOR RECEIVING AND ANALYSING A SAMPLE" and filed on Feb. 26, 2016, the contents of which are hereby incorporated herein by reference in their entireties for all purposes, and which in turn claims priority to GB Application Serial No. 1503364.0, filed on Feb. 27, 2015.

BACKGROUND

An impression left by the friction ridges of human skin, such as the skin of a human finger contains information regarding the identity of the human. It is widely known that the appearance of the impression of the human finger, known as a fingerprint, is unique to each human and may be used to confirm the identity of the human. The appearance of the impression of the skin of other human body parts may also be unique to each human and so may also be used to confirm the identity of the human. Such impressions of human skin, when not specific to the skin of the human finger, may be called skin-prints.

In addition to the appearance of the impression left by human skin, the impression may contain chemical species which themselves may be detected in order to obtain further information.

For example, when a human intakes a substance (e.g. by ingestion, inhalation or injection) the substance may be metabolised by the human body giving rise to secondary substances known as metabolites. The presence of a particular metabolite can be indicative of a specific intake substance. The intake substance and/or metabolites may be present in sweat and, as such, may be left behind in a skin-print, e.g. a fingerprint. Detection of such metabolites in a skin-print can be used as a non-invasive method of testing for recent lifestyle activity such as (but not limited to) drug use, or compliance with a pharmaceutical or therapeutic treatment regime.

Importantly, the taking of a skin-print is much simpler than obtaining other body fluids such as blood, saliva and urine, and is more feasible in a wider range of situations. Not only this but since the appearance of the skin-print itself provides confirmation of the identity of the person providing the skin-print, there can be greater certainty that the substance or substances in the skin-print are associated with the individual. This is because substitution of a skin-print, particularly a fingerprint, is immediately identifiable from appearance whereas substitution of, for example, urine, is not immediately identifiable from appearance. As such, testing for one or more substances in a skin-print provides a direct link between the one or more substances and the identity of the human providing the skin-print.

It is important, therefore, that a substrate on which a skin-print is collected cannot be contaminated (either innocently or maliciously) before or after the impression of the skin is taken. The substrate must be accessible only for the short period during which the skin-print is taken.

It is also desirable for metabolite detection not only to be reliable but also to be simple, efficient and user-friendly.

Furthermore, since a volume of metabolite that, if present, might be expected in a fingerprint is likely to be of the order of microliters, it is desirable to maximise the proportion of the skin-print that is analysed in order to maximise accuracy of the test.

STATEMENTS OF INVENTION

Against this background, there is provided a device for receiving and analysing a sample, wherein the analysing involves use of a solution, the device comprising:
   a sample receiving portion for receiving a sample to be analysed;
   a solution capsule having a sealed configuration in which the solution capsule is sealed and a release configuration in which contents of the solution capsule are released via a flow path that provides fluid communication between the solution capsule and the sample receiving portion; and
   a bistable release mechanism comprising an actuator wherein the bistable release mechanism releases only in the event that a force applied to the actuator reaches a threshold force and wherein actuation of the actuator results in one-way conversion of the solution capsule from the sealed configuration into the release configuration.

In this way, a skin-print, most likely a fingerprint, may be securely received and reliably analysed for presence of one or more chemical species.

In a further aspect, there is provided a device for receiving and analysing a sample, wherein the analysing involves use of a solution, the device comprising:
   a first sample receiving portion comprising a wicking material for receiving a sample to be analysed using the solution; and
   a second sample receiving portion comprising a non-porous substrate.

In this way, the device may be used to collect two skin-prints, most likely two fingerprints, one for chemical analysis and another for optical analysis.

BRIEF DESCRIPTION OF THE DRAWINGS

Specific embodiments of the invention will now be described, by way of example only, with reference to the accompanying drawings in which.

SPECIFIC DESCRIPTION

First Embodiment

Figure 1:
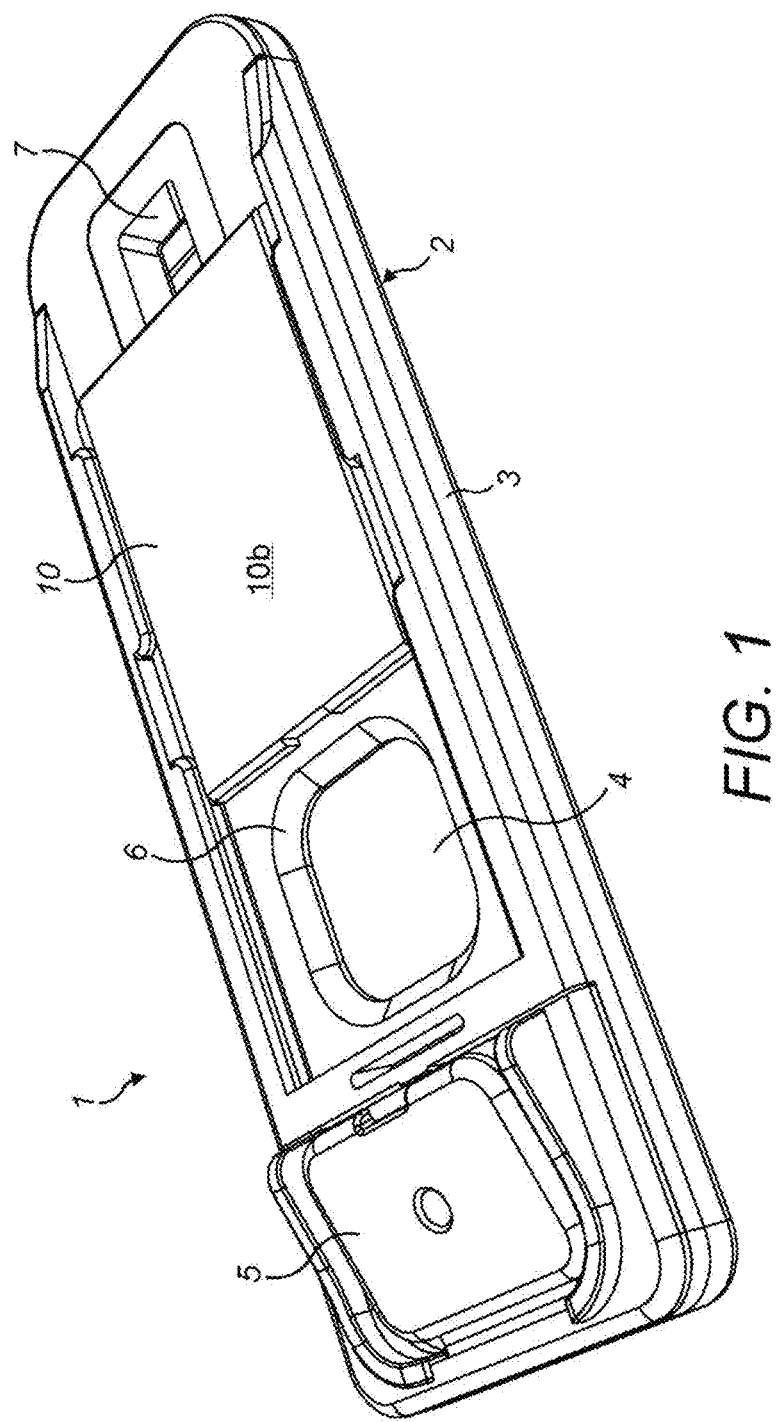
FIG. 1 shows a perspective view of device in accordance with a first embodiment of the invention.
Figure 2:
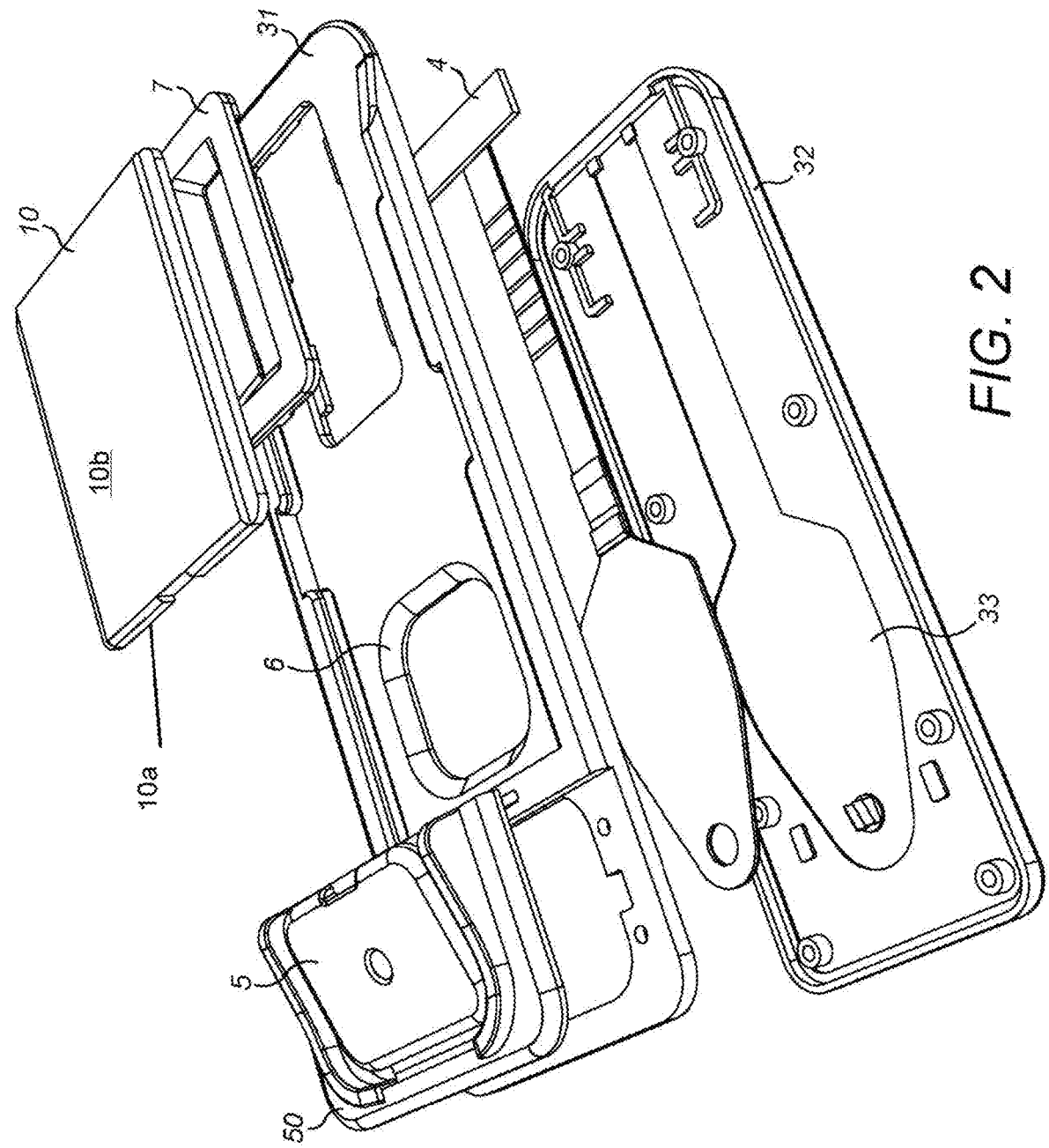
FIG. 2 shows an exploded view of the device of FIG. 1.

In accordance with a first embodiment, as shown in FIG. 1, there is a device 1 for receiving and analysing a sample. The first embodiment is shown in an exploded view in FIG. 2.

The device comprises a housing 2 and a sample receiving material in the form of a substrate 4 that is located within the housing 2. The housing 2 comprises a body 3 having an upper portion 31 and a lower portion 32. The lower portion 32 comprises an indentation 33 that reflects a shape of the substrate 4. The housing 2 also comprises a solution capsule assembly 50 comprising a solution capsule 5. The housing 2 further comprises a sample window 6 that bounds a skin-print receiving region 42 of the substrate 4. The dimensions of the sample window 6 may be configured to allow receipt of at least a part of an area of a skin-print, such as a fingerprint. The housing 2 further comprises a result window 7 and a shutter 10 that is slidable relative to the body 3.

The substrate 4 is of a porous, wicking material, such as Fusion 5™. The frangible enclosing member 54 of the solution capsule 5 is of a laminar material comprising a layer of polypropylene and a layer of aluminium. The solution capsule assembly 50 (except for the frangible enclosing member 54) is of polypropylene. The remaining components of the housing 2 are of high density polystyrene (HDPS).

The laminar material comprising a layer of polypropylene and a layer of aluminium is selected such that it pierces cleanly and predictably.

Figure 3:
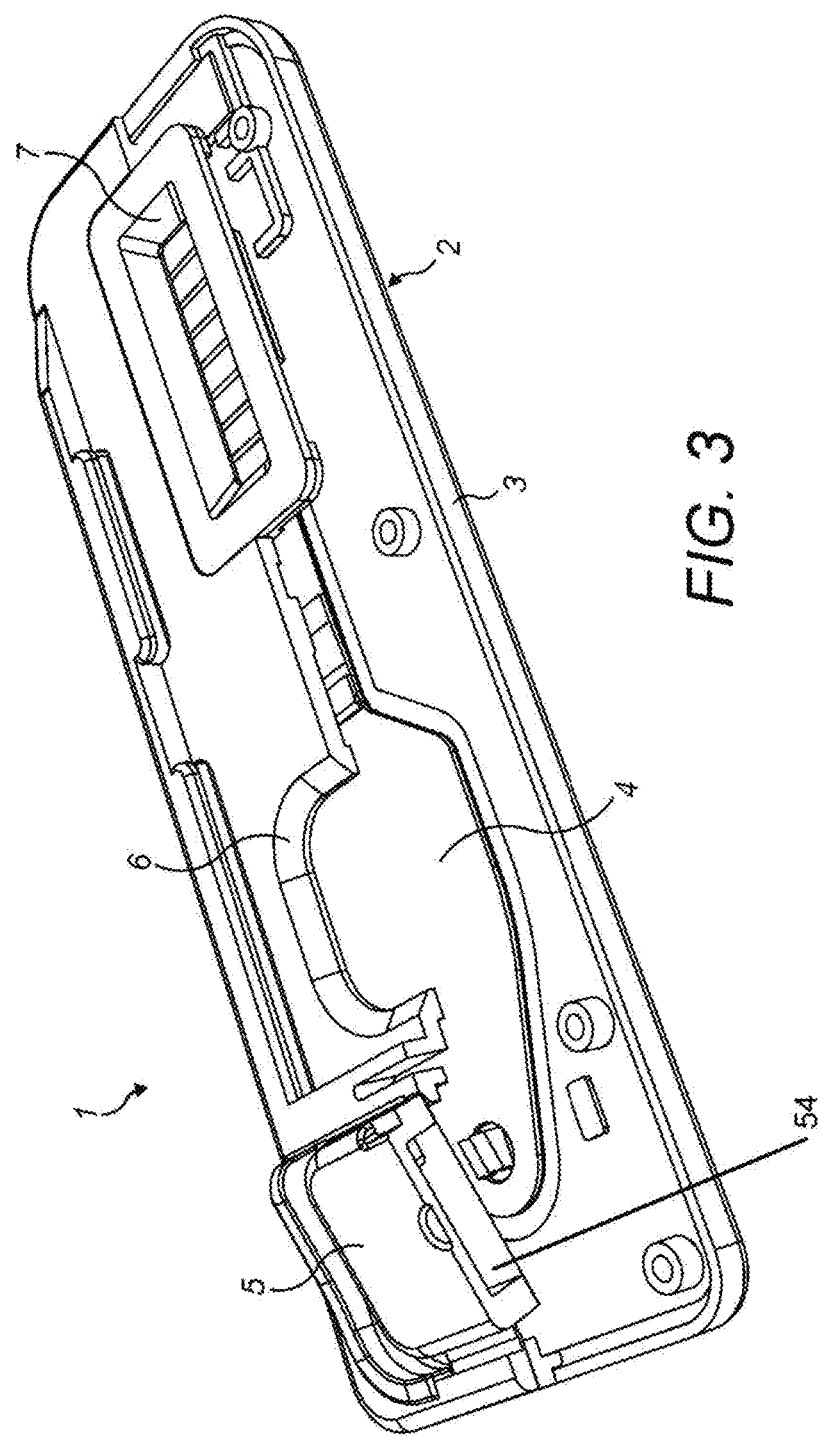
FIG. 3 shows a perspective view of the device of FIG. 1 with some of the components removed and others part cut away so as to show internal features.

The device 1 of FIG. 1 is shown again in FIG. 3 with the upper body portion 31 and the solution capsule assembly 50 shown in cross-section and with the shutter 10 removed altogether. This renders some of the internal features more visible than in FIG. 1.

The substrate 4 is mounted in the housing 2 and is in a fixed position relative to the housing 2. The housing 2 is intended to protect the substrate 4. The housing may be opaque in order to protect substances that are susceptible to photodegradation which may be present on the substrate 4.

Figure 4:
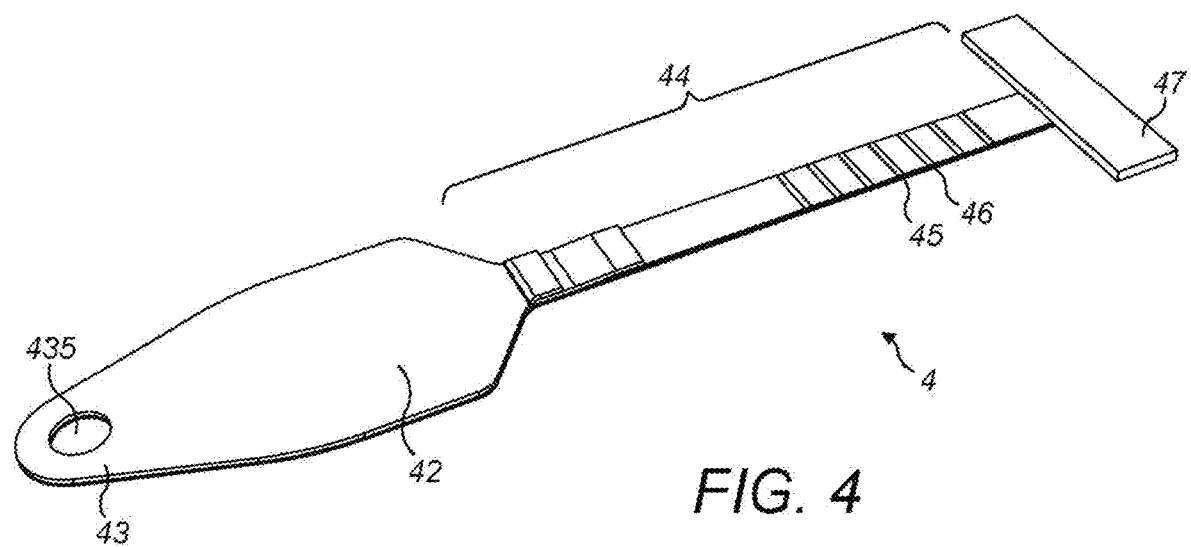
FIG. 4 shows a perspective view of a lateral flow substrate that is present within the device of FIG. 1.

The substrate 4, shown in isolation in FIG. 4, comprises the skin-print receiving region 42, a solution-receiving region 43 and an analysis region 44. The analysis region 44 comprises a result line 45 and a control line 46, both of which are located within the result window 7. The analysis region 44 further comprises an absorbent solution sink 47, downstream of the result line 45 and control line 46, which simply acts to soak up fluid that has already passed through the previous parts of the lateral flow test. The solution-receiving region 43 of the substrate 4 may comprise an aperture 435.

The solution receiving region 43 of the substrate 4 is of variable width. In the vicinity of the aperture 435 the solution receiving region 43 is at its narrowest. With distance towards the skin-print receiving region 42, the width of the solution-receiving region 43 increases.

The solution-receiving region 43 may have a portion of constant width and a portion of narrowing width towards the analysis region 44. The analysis region 44 may be of constant width. The width of the absorbent sink 47 may again be wider.

The shutter 10 comprises an inside 10a that faces inwardly towards the substrate and an outside 10b which faces outwardly. The shutter 10 may further comprise a gripping feature (not shown) on the outside 10b of the shutter to assist in sliding of the shutter 10.

The shutter 10 is movable with respect to the body 3 from a first position, to a second position and into a third position.

In the first position (shown in FIG. 16), the sample window 6 is covered by the shutter 10 and the result window 7 is not covered by the shutter 10. In the second position (shown in FIG. 1), the sample window 6 is not covered by the shutter 10 and the result window 7 is covered by the shutter 10. In the third position (which appears the same as the first position, shown in FIG. 16), the sample window 6 is again covered by the shutter 10 and the result window 7 is not covered by the shutter 10.

Viewed from the outside, therefore, in the case of the illustrated embodiment, it may be that the first and third positions appear identical. However, the third position is different from the first position in that, once in the third position, the shutter cannot again be moved into the second position.

In this way, if a user receives the device 1 of the first embodiment in a configuration where the sample window 6 is covered by the shutter 10, the user will attempt to move the shutter 10 into the second position. If this is not possible, this is because the shutter 10 is already in the third position. Accordingly, the device 1 is not usable since the skin-print receiving region 42 bounded by the sample window 6 is inaccessible. This prevents reuse of an already-used device 1 or use of a device 1 that may have been subject to tampering (and hence possible contamination that may influence a result to be obtained using the device).

On the other hand, if it is possible for a user to move the shutter 10 into the second position, this indicates to the user that the device 1 has not been used previously and that the skin-print receiving region 42 bounded by the sample window 6 has not previously been exposed.

The third position being different from the first position may be achieved by one or more internal snap-fit features that prevent the shutter from moving back to the first position following the second position and also retain the shutter in the third position.

The sample window 6 comprises an aperture in the body 3 of the housing 2, such that the sample window 6 bounds the skin-print receiving region 42. The sample window 6 and hence the skin-print receiving region 42 are only accessible when the shutter 10 is in the second position.

At least a part of the analysis region 44 of the substrate 4 is bounded by the result window 7.

Figure 9:
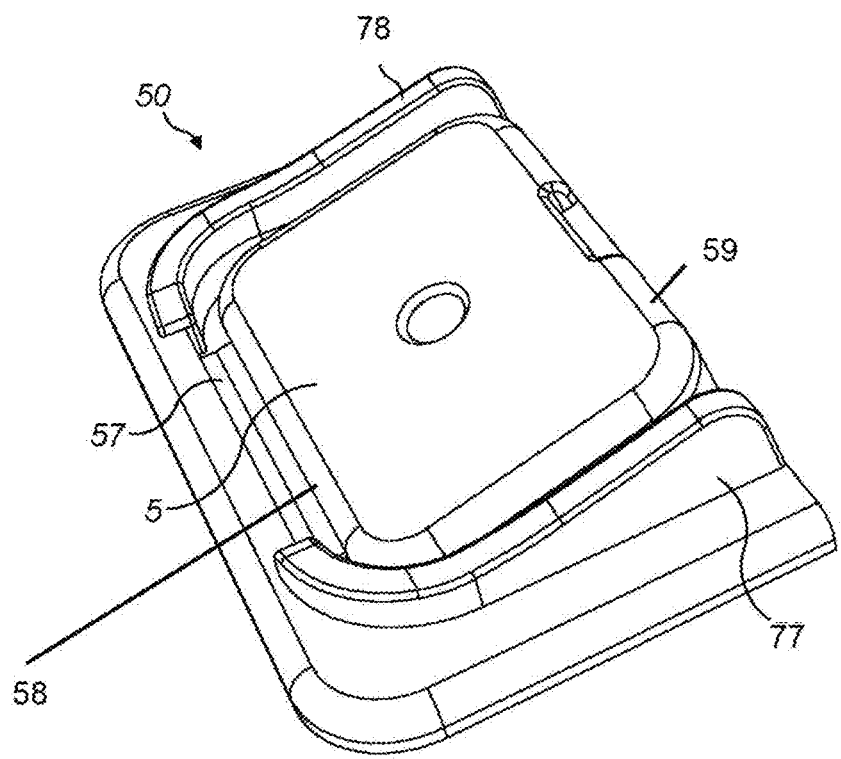
FIG. 9 shows the capsule assembly of the device of FIG. 1 with the capsule in an initial configuration.
Figure 10:
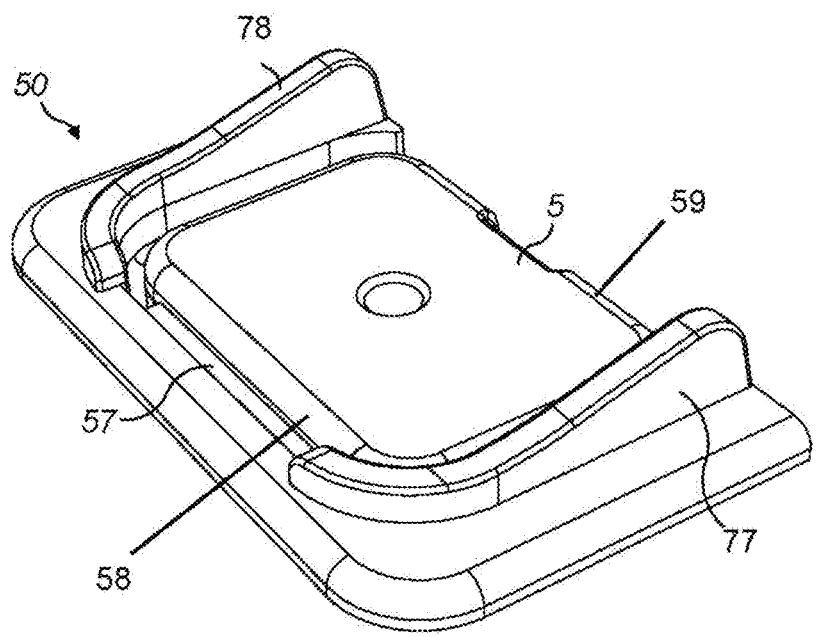
FIG. 10 shows the capsule assembly of the device of FIG. 1 with the capsule in a subsequent configuration

The solution capsule assembly 50 (see FIGS. 9 and 10) comprises a capsule surround 56, a hinge 57 and a solution capsule 5. The capsule surround 56 is attached to the upper portion 31 of the base 3 via locating pins (680) on the underside of the capsule surround (see FIG. 18) that are received into corresponding locating sockets (380) in the base 3 (see FIG. 13). The solution capsule 5 is connected to the capsule surround 56 via the hinge 57. The capsule surround 56 comprises a pair of ramped guard portions 78, 77 that sit on opposite sides of the capsule surround 56. The ramped guard portions 78, 77 act to prevent access to the sides of the capsule 5 and also to prevent movement of the capsule 5 with respect to the capsule surround 56 by an object that is larger than the distance between the ramped guard portions 78, 77.

Figure 5:
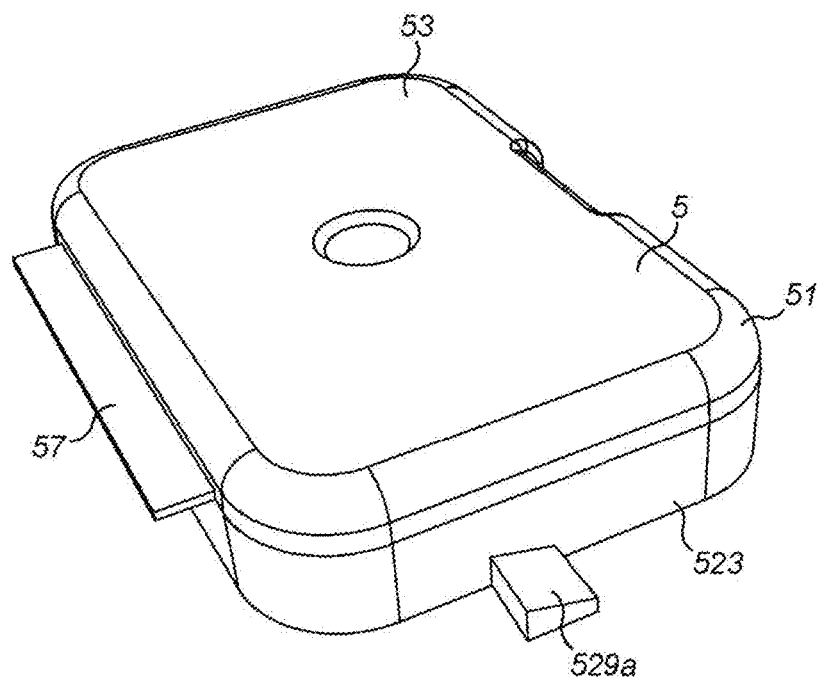
FIG. 5 shows a solution capsule of the device of FIG. 1.

The capsule 5, shown in isolation in FIG. 5, comprises a substantially rigid cup portion 51 having sidewalls 521, 522, 523, 524 and a substantially planar base 53. Together, the sidewalls 521, 522, 523, 524 and planar base 53 provide a cup-shaped reservoir with an open end substantially opposite the planar base 53. The solution capsule 5 further comprises a frangible enclosing member 54 that is fastened to or proximate to a perimeter of the open end of the cup portion 51 so as to seal the open end. In this way, a solution in the cup portion 51 can be sealed within the solution capsule 5 once the frangible enclosing member 54 seals the open end of the cup portion 51. Alternatively, the solution may be injected into the capsule 5 after the frangible enclosing member 54 has already sealed the open end of the cup portion 51.

With the exception of the frangible enclosing member 54, the solution capsule assembly 50 (that comprises the capsule surround 56, hinge 57 and solution capsule 5) may be moulded of a single piece.

Figure 6:
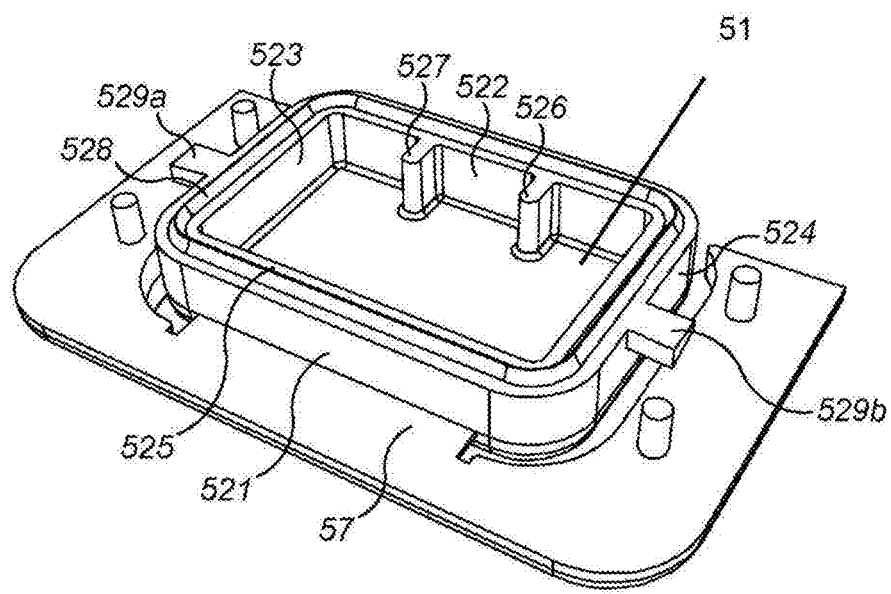
FIG. 6 shows the solution capsule of FIG. 5 with a surface removed, revealing internal features.

FIG. 6 shows the rigid cup portion 51 of the solution capsule 5. The sidewalls of the rigid cup portion 51 comprise first, second, third and fourth sidewalls, 521, 522, 523, 524. The first and second sidewalls 521, 522 are substantially of equal length and are mutually parallel. The third and fourth sidewalls 523, 524 are substantially of equal length and are mutually parallel. The first and second sidewalls 521, 522 are longer than the third and fourth sidewalls 523, 524. The first and second sidewalls 521, 522 are perpendicular to the third and fourth sidewalls 523, 524. The hinge 57 is adjacent the first sidewall 521.

The open end of the sidewalls comprises a sealing surface 525 that is largely perpendicular to a major surface of each of the respective sidewalls 521, 522, 523, 524. The frangible enclosing member 54 (not shown) is fastened to the sealing surface 525 by a fastening that comprises a continuous weld seal. The sealing surface, prior to receiving the frangible enclosing member 54, comprises an upstanding portion 528 having a triangular cross section. The upstanding portion 528 is configured to melt into the frangible enclosing member 54 during a process in which the frangible enclosing member 54 is welded to the sealing surface 525.

The polypropylene layer of the frangible enclosing member 54 is orientated adjacent the polypropylene upstanding portion 528 of the polypropylene capsule assembly 50 in order that the two facing polypropylene surfaces melt together under a heat welding process.

The second sidewall 522 comprises a pair of projecting elements 526, 527 that project inwardly from the second sidewall 522 that is opposite the hinge 57. The pair of projecting elements 526, 527 is substantially mutually parallel.

The housing 2 comprises a recess 60 (see FIG. 8) that comprises an upper portion that is situated in the solution capsule assembly 50 and a lower portion that is situated in the upper portion 31 of the body 3.

Figure 8:
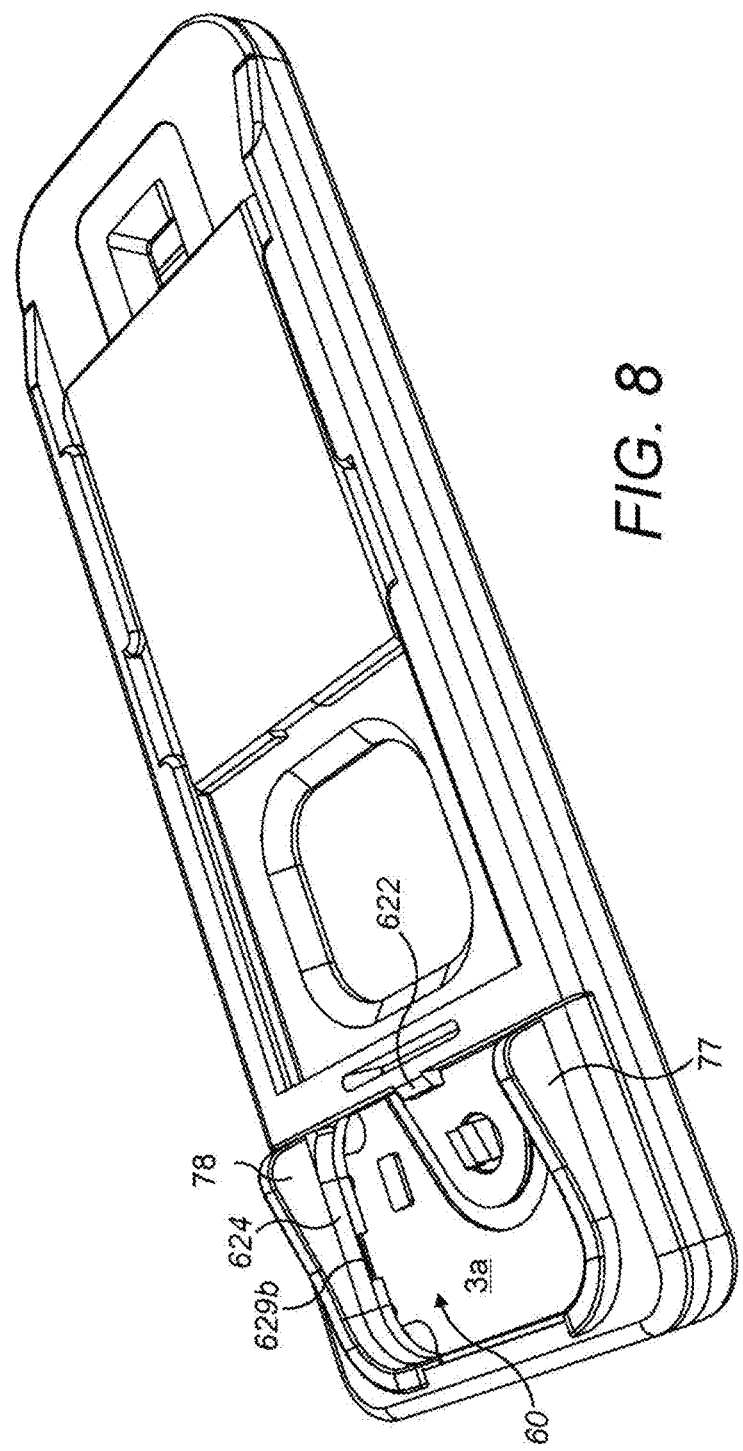
FIG. 8 shows the device of FIG. 1 with a capsule removed.

The device 1 is shown in FIG. 8 with the capsule 5 of the solution capsule assembly 50 removed to show more clearly the recess 60 in which the solution capsule sits.

The recess 60 comprises sidewalls 621, 622, 623, 624 that are dimensioned slightly larger than the sidewalls 521, 522, 523, 524 of the cup portion 51 of the solution capsule 5. The sidewalls 621, 622, 623, 624 of the recess 60 comprise first, second, third and fourth sidewalls, 621, 622, 623, 624. The first and second sidewalls 621, 622 are substantially of equal length and are mutually parallel. The third and fourth sidewalls 623, 624 are substantially of equal length and are mutually parallel. The first and second sidewalls 621, 622 are longer than the third and fourth sidewalls 623, 624. The first and second sidewalls 621, 622 are perpendicular to the third and fourth sidewalls 623, 624. The first, second, third and fourth sidewalls 621, 622, 623, 624 of the recess 60 are, respectively, adjacent and parallel to the first, second, third and fourth sidewalls, 521, 522, 523, 524 of the capsule 5. The hinge 57 is adjacent the first sidewall 621.

The recess 60 also comprises a base 3a that is formed of a surface of the body 3, in particular an internal surface of the lower portion 32 of the body 3.

The depth of the sidewalls 621, 622, 623, 624 of the recess 60 is similar to the depth of the sidewalls 521, 522, 523, 524 of the cup portion 51. Since the solution capsule assembly 50 is fixedly attached to the upper portion 31 of the body 3, the solution capsule 5 is pivotally mounted to the body 3 via the hinge 57 and the capsule surround 56. The orientation of the solution capsule 5 is such that the frangible enclosing member 54 faces the base 3a.

Figure 12:
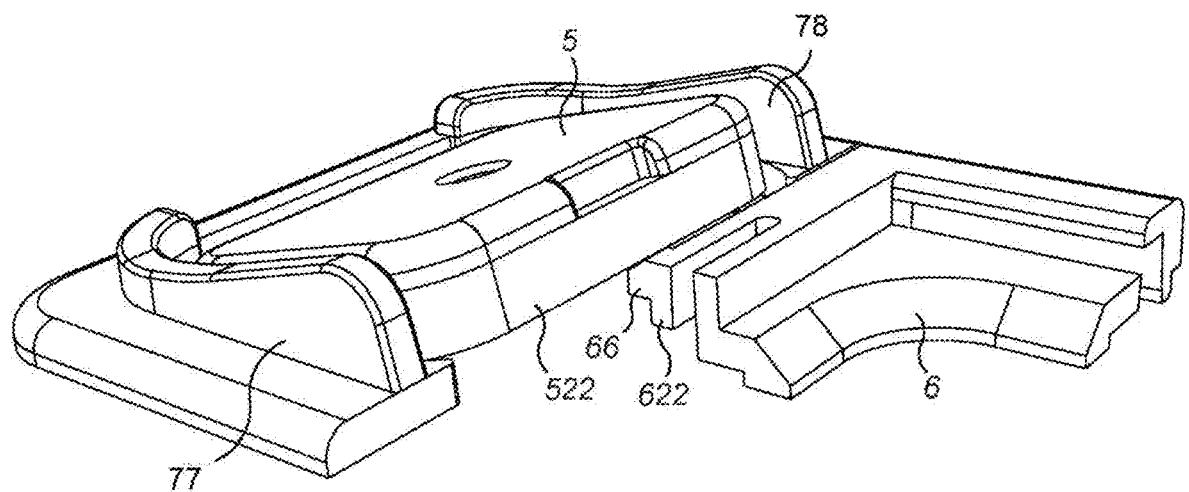
FIG. 12 shows a view of parts of the device of FIG. 1 with the capsule in the initial configuration.

At a second sidewall 622 of the recess 60, opposite the first sidewall 621 of the recess 60, the recess 60 comprises a protrusion 66 that protrudes from an interior of the second sidewall 622. The protrusion 66 (see FIG. 12) extends from the second sidewall 622 of the recess 60 towards an interior of the recess 60. A dimension between the first sidewall 621 of the recess 60 and an inmost surface of the protrusion 66 is slightly smaller than a corresponding external dimension of the solution capsule 5 (e.g. the distance between the first sidewall 521 of the solution capsule 5 and the second sidewall 522 of the solution capsule 5).

At a lower end of the third and fourth sidewalls 623, 624 of the recess 60 is a protrusion 629a, 629b.

Figure 11:
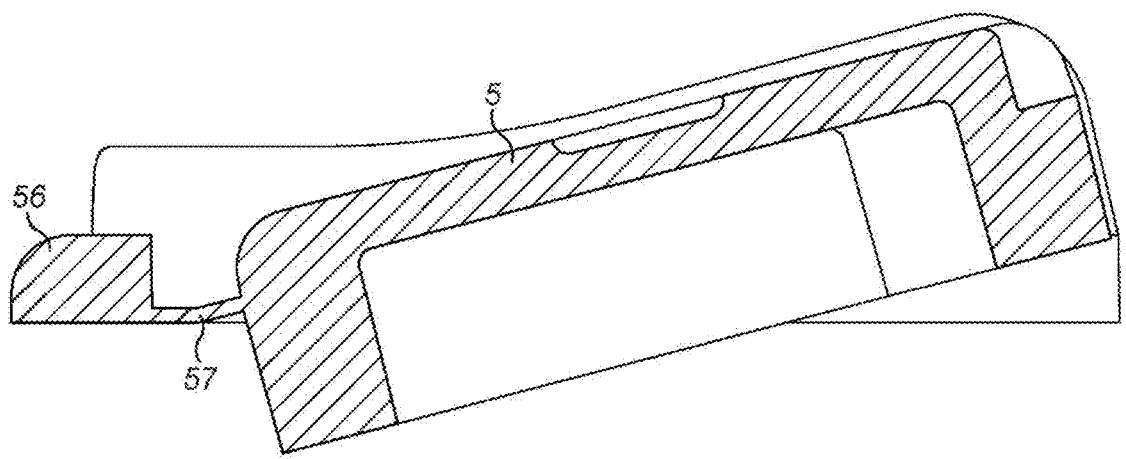
FIG. 11 shows a cross sectional view of the capsule assembly with the capsule in the initial configuration.

In an initial configuration of the solution capsule 5 (see, for example, FIGS. 9 and 11), a first end 58 of the solution capsule 5 adjacent the first sidewall 521 of the solution capsule 5 substantially does not protrude above the first sidewall 621 of the recess 60 at a first end 68 of the recess 60. Also in the initial configuration, a second end 59 of the solution capsule 5 adjacent the second sidewall 522 of the solution capsule 5 sits substantially proud of the second sidewall 621 of the recess 60 at a second end 69 of the recess 60. The second end 59 of the solution capsule 5 sits proud of the second sidewall 622 of the recess 60 since the protrusion 66 restricts movement of the second end of the solution capsule 5 into the second end of the recess 69. As such, though the frangible enclosing member 54 faces the base 3a, the frangible enclosing member 54 is not parallel with the base 3a. Rather, the frangible enclosing member 54 is inclined from the first end of the capsule to the second end of the solution capsule 5.

The location and dimension of the protrusion 66 are configured to allow the second end 59 of the solution capsule 5 to move into the second end 69 of the recess 60 (by rotation about the hinge 57) only once a specified threshold force has been applied to the second end 59 of the substantially planar base 53 of the solution capsule 5 in order to overcome resistance to such movement that is provided by the protrusion 66. This may be known in the art as a slip latch. The threshold force may, for example, be 10 Newtons. A subsequent configuration of the solution capsule 5 (that is, subsequent to the initial configuration of the solution capsule 5) is achieved once the specified threshold force has been applied such that the resistance to movement has been overcome and so the second end 59 of the solution capsule 5 moves into the recess 60. In this subsequent configuration, shown in FIG. 10, the frangible enclosing member 54 may be substantially parallel to the base 3a.

Figure 18:
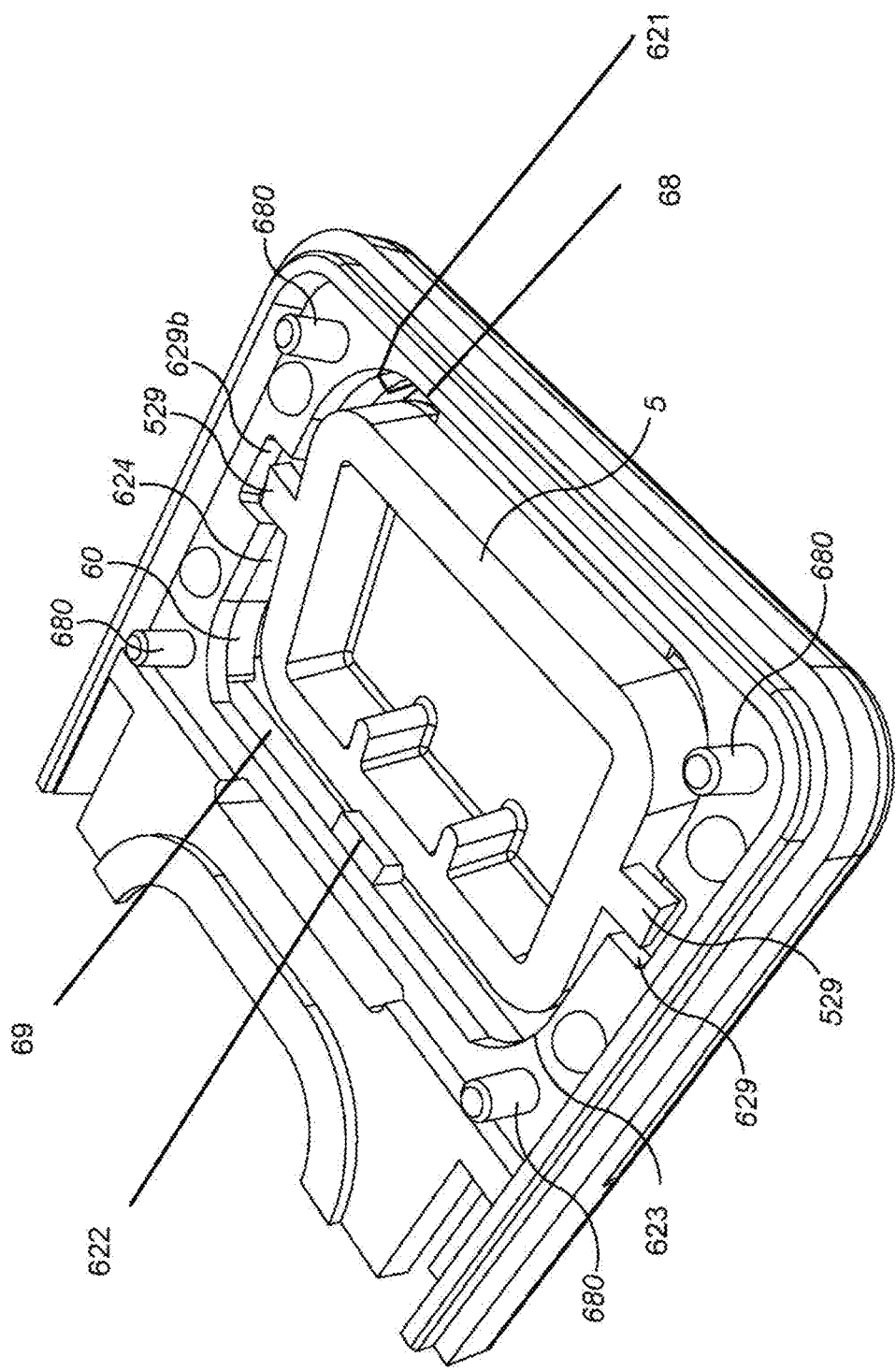
FIG. 18 shows a part of the device of FIG. 1 from an internal perspective.

As evident in FIG. 6, the solution capsule 5 comprises a pair of ears 529a, 529b. The ears 529a and 529b extend outwards from the third and fourth walls 523, 524 of the capsule 5 such that a dimension from an outer end of one ear 529a to an outer end of the other ear 529b is wider than the width of the recess 60. The ears 529a, 529b of the solution capsule 5 are located such as to be received within the protrustions 629a, 629b, respectively, of the recess 60, as shown in FIG. 18. Accordingly, the ears 529a, 529b prevent the solution capsule 5 from being lifted relative to the capsule surround 56.

Figure 13:
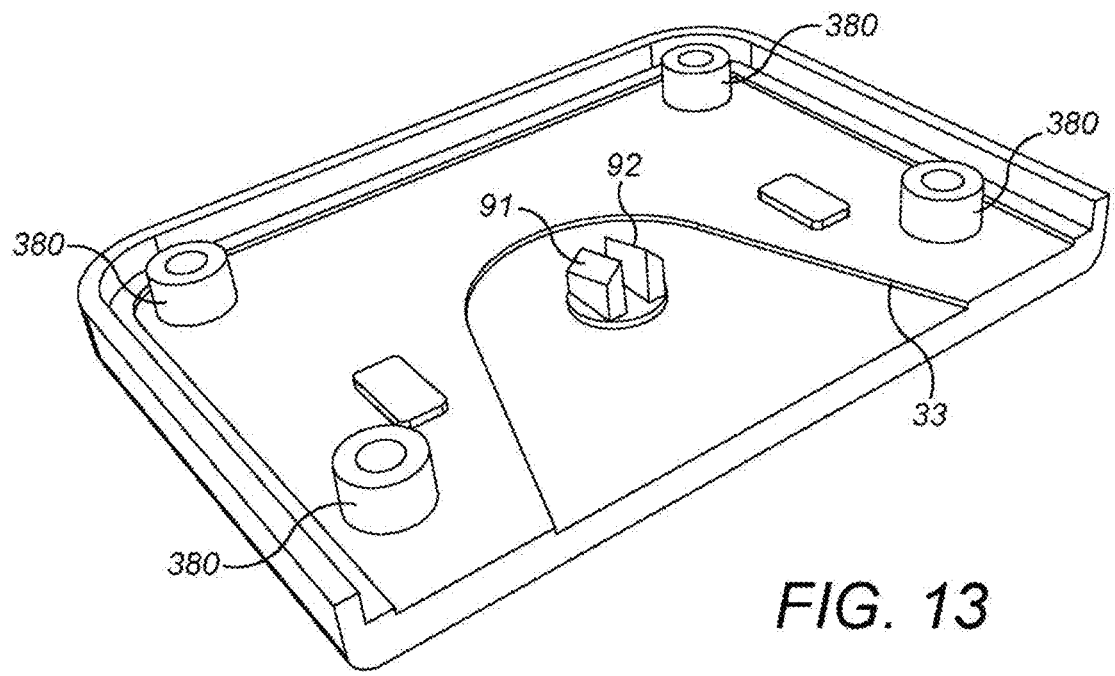
FIG. 13 shows an enlarged view of parts of the device of FIG. 1, centred on a pair of piercers which are a constituent part of the device.
Figure 14:
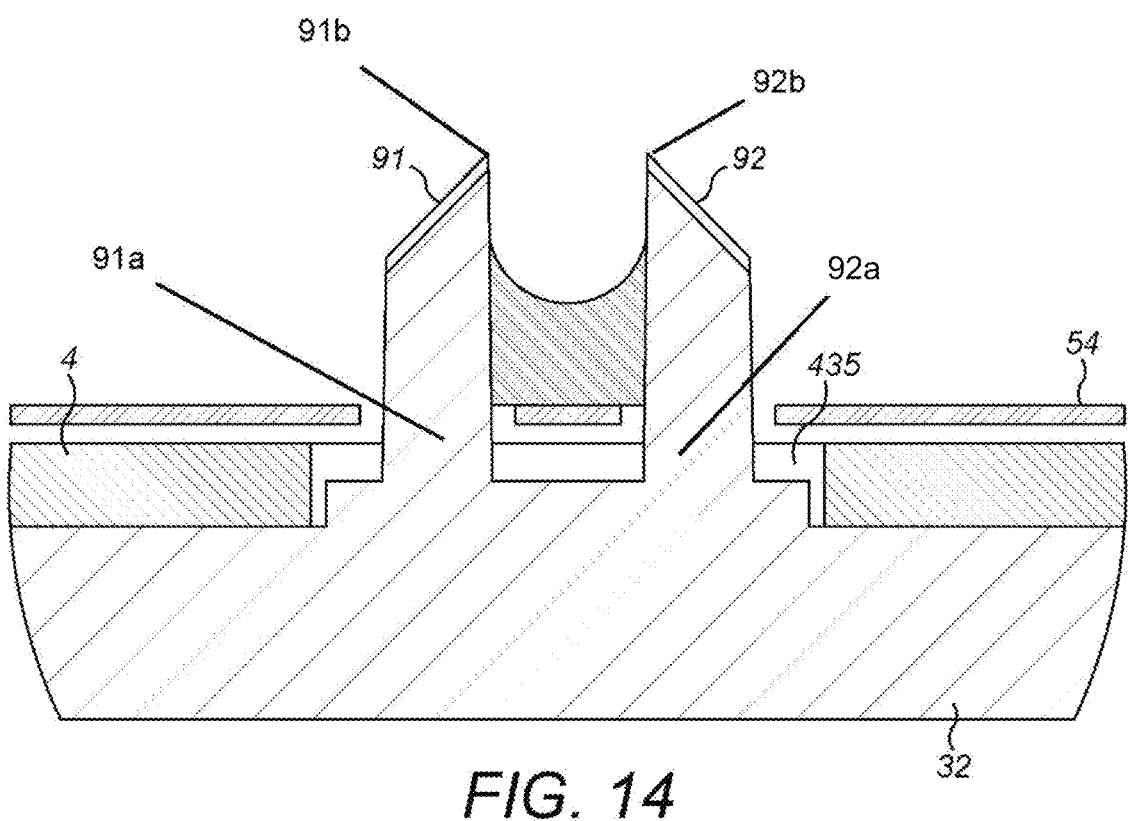
FIG. 14 shows a cross-sectional view of the pair of piercers.

The body 3 further comprises a pair of piercers 91, 92 (see FIGS. 13 and 14). In the first embodiment, the piercers are spaced apart by a distance of approximately 1 mm. Each of the two piercers 91, 92 comprises a proximal end 91a, 92a and a distal end 91b, 92b. The proximal end 91a, 92a of each piercer is fastened to, or otherwise projects from, the base 3a within recess 60. The proximal end 91a, 92a of each piercer may be substantially central relative to the sidewalls 621, 622, 623, 624 of the recess 60. The distal end 91b, 92b of each piercer sits proud of the base 3a within recess 60. The distal end 91b, 92b of each piercer comprises a piercing feature or piercing profile such as an acute shape.

The location of the piercers 91, 92 is such that, in the initial configuration of the solution capsule 5, the piercers are distant from the frangible enclosing member 54 of the capsule 5 and such that, in the subsequent configuration of the solution capsule 5, the piercers project through (thereby piercing) the frangible enclosing member 54 of the capsule 5.

The substrate 4 is parallel to the base 3a of the body 3. The aperture 435 in the solution-receiving region 43 of the substrate 4 surrounds the pair of piercers 91, 92.

Use of the device will be described in detail below. However, features of the piercers 91, 92 are dictated, in part, by their required functionality. Accordingly, the following paragraph describes some aspects of the device 1 in use in order to illustrate features of the piercers 91, 92. These aspects of the piercers are illustrated in FIG. 14.

A distance between the piercers 91, 92 is configured such that, when the buffer capsule 5 enters the subsequent configuration (such that the frangible enclosing member 54 is pierced in the regions of each of the two piercers 91, 92), solution present in the buffer capsule 5 is drawn between the two piercers 91, 92 and, by virtue of a surface tension present on the solution between the two piercers 91, 92, a capillary pull action results which draws a drop of solution out of the buffer capsule 5 to be absorbed by the solution-receiving region 43 of the substrate 4 that surrounds the pair of piercers 91, 92. Immediately after the drop of solution is released from between the two piercers 91, 92, there is an absence of solution between the two piercers 91, 92 which allows the opportunity for ambient air to enter the buffer capsule 5 in order to equalise pressure inside and outside the buffer capsule 5. Once the pressure is equalised, a further drop of solution is drawn between the two piercers 91, 92 and the same process is repeated.

Figure 7:
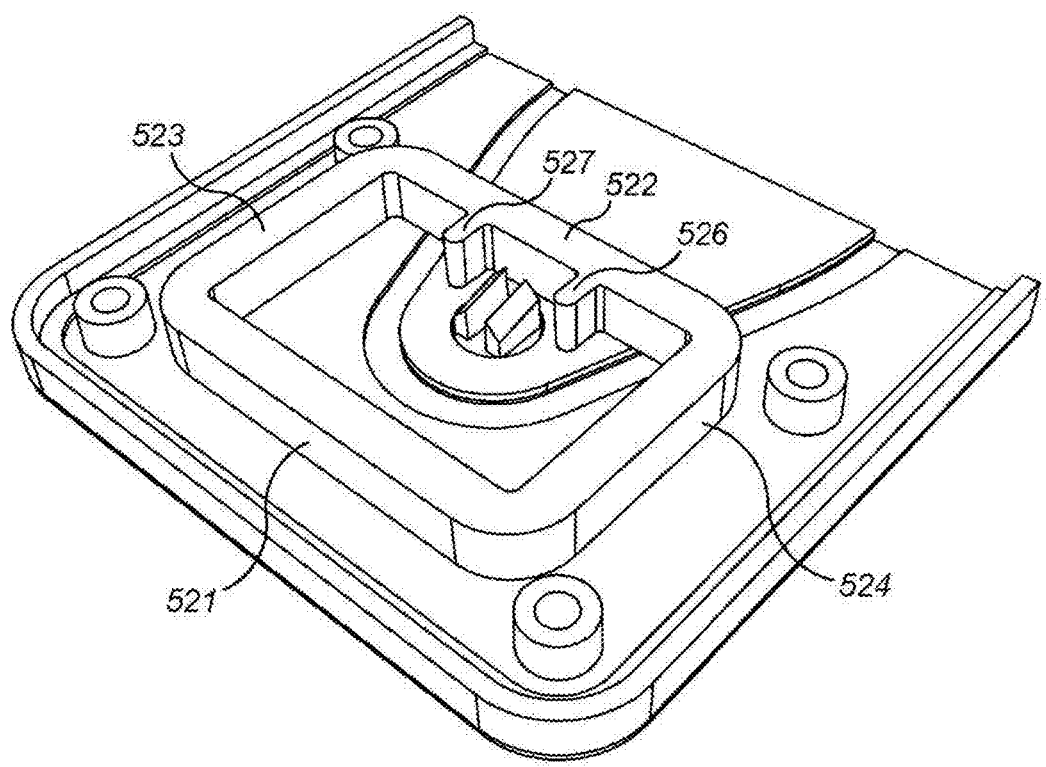
FIG. 7 shows a part of the capsule of FIG. 5 relative to other components of the device.

The pair of piercers 91, 92 is located relative to the solution capsule 5 such that the pair of piercers 91, 92 is aligned with an area of the frangible enclosing member 54 that is within an area between the pair of projecting elements 526, 527 that project inwardly of the second sidewall 522. (This relationship is clear from FIG. 7, in which various components, including the frangible enclosing member 54, are removed for clarity.) Consequently, when, in use (as described further below), the piercers 91, 92 pierce the frangible enclosing member 54, the strain force on the weld is reduced which prevents the weld from failing as a consequence of transverse forces.

Furthermore, the pair of piercers 91, 92 is located relative to the solution capsule 5 such that the location of the flow path out of the solution capsule 5 once the piercing occurs is precisely known.

Since the substrate 4 comprises a wicking material that draws (or wicks) solution, solution received on the solution-receiving region 43 is drawn from that region towards the skin-print receiving region 42 and onward to the analysis region 44.

The substrate 4 (see FIG. 4) may be configured for a lateral flow analysis, which is known in the art. The following is a brief explanation of the lateral flow method in the context of the present embodiment. Variations on this lateral flow technique fall within the scope of the claimed invention.

Lateral flow immunoassays are simple tests for rapid detection of the presence or absence of a target analyte in a sample for home testing, point of care testing, or laboratory applications. Lateral flow devices preferably utilise a solid support through which a mobile phase (e.g., a buffer solution) can flow through by capillary action to a reaction matrix where a detectable signal, such as colour changes or colour differences at a test site, may be generated to indicate the presence or absence of the target analyte. As used herein, the term "capillary action" refers to the process by which a molecule is drawn across the lateral test device due to such properties as surface tension and attraction between molecules.

The lateral flow device as described herein is for use in an immunoassay i.e. a method for analysing a sample comprising from 0.1 pg to 1 µg of analyte. The immunoassay comprises a competitive binding assay, where any labelled probe (e.g. antibody) not bound to analyte provides an identifiable signal in the test site whilst any labelled probe bound to analyte, e.g. in the form of an immunocomplex, passes through the test site and does not provide an identifiable signal in the test site. As the number of analyte molecules present in the sample increases, the amount of unbound labelled probe passing through the test site decreases. Thus the higher the level of analyte in the sample, the weaker the identifiable signal at the test site will be. Such a device/method allows qualitative tests to be undertaken, i.e. whether or not the sample contains an analyte of interest. Such a device/method also may allow quantitative tests to be undertaken by measuring the intensity of the signal at the test site, whereby the higher the intensity of the signal, the lower the amount of analyte in the sample.

In the context of the first embodiment, movement of the solution capsule 5 into the subsequent configuration results in solution being released in a controlled fashion onto the solution receiving region 43. Solution is drawn (wicked) down the substrate towards the skin-print receiving region 42. The solution is selected to dissolve chemical species that may be present in the skin-print receiving region 42, such as an analyte of interest that may be present in a skin-print on the skin-print receiving region 42. The solution (which may or may not now include the analyte of interest) continues to be drawn down the substrate 4 into the analysis region 44. The analysis region 44 of the substrate 4 may have a reduced width by comparison with the skin-print receiving region 42, to assist in concentrating the solution into a smaller area. The analysis region 44 comprises a competitive binding assay having a label. If present, the analyte of interest will bind to the labelled assay. The label may comprise a fluorescent tag. The analysis region 44 further comprises the result line 45 that is located within the result window 7. The result line 45 comprises a further molecule, a protein-analyte conjugate, which is fixed in position (immobilised) on the substrate 4. The protein-analyte conjugate is chosen to bind with the assay in the event that the assay has not already been bound to the analyte of interest. Hence, if the analyte of interest is present, all available assay binding sites are occupied, the further molecule cannot bind with the assay and so the assay passes through. If, however, the analyte of interest is absent, the further molecule binds with the assay which is then fixed in position on the substrate. Since the assay is labelled, once sufficient assay is fixed in position, the label becomes apparent through, for example, a change in colour. That is to say, the result line 45 appears to change colour. The label may be fluorescent.

In addition to the result line 45, there may also be a control line 46. The control line 46 may be configured to capture a control assay that is present in the buffer solution. The purpose of the control line 46 may be to show that the reaction conditions were as expected even when the result line 45 does not change colour (indicating that an insufficient presence of the analyte of interest).

It will be apparent that, for an appropriate sensitivity to a particular analyte, a specific volume of the solution used to dissolve the skin-print must be used. The device 1 may be supplied with the specific volume of solution in the solution capsule 5. Moreover, the solution capsule 5 and solution release mechanism need to be configured in order to ensure that all of the specific volume of solution is released and that none of the specific volume of solution remains in the solution capsule 5 at the conclusion of the test. Furthermore, the solution release mechanism needs to be configured in such a way as to release the solution in a predictable flow rate, in order to maximise efficiency of bonding.

The device of the illustrated embodiment is approximately 92 mm in length, 32 mm in width and 6 mm in thickness, increasing to 9.5 mm in thickness in the region of the solution capsule assembly. The sample window 6 is approximately 15 mm×15 mm. Other dimensions are possible and fall within the scope of the appended claims.

First Embodiment in Use

The following section describes the first embodiment of the device, in use.

Figure 16:
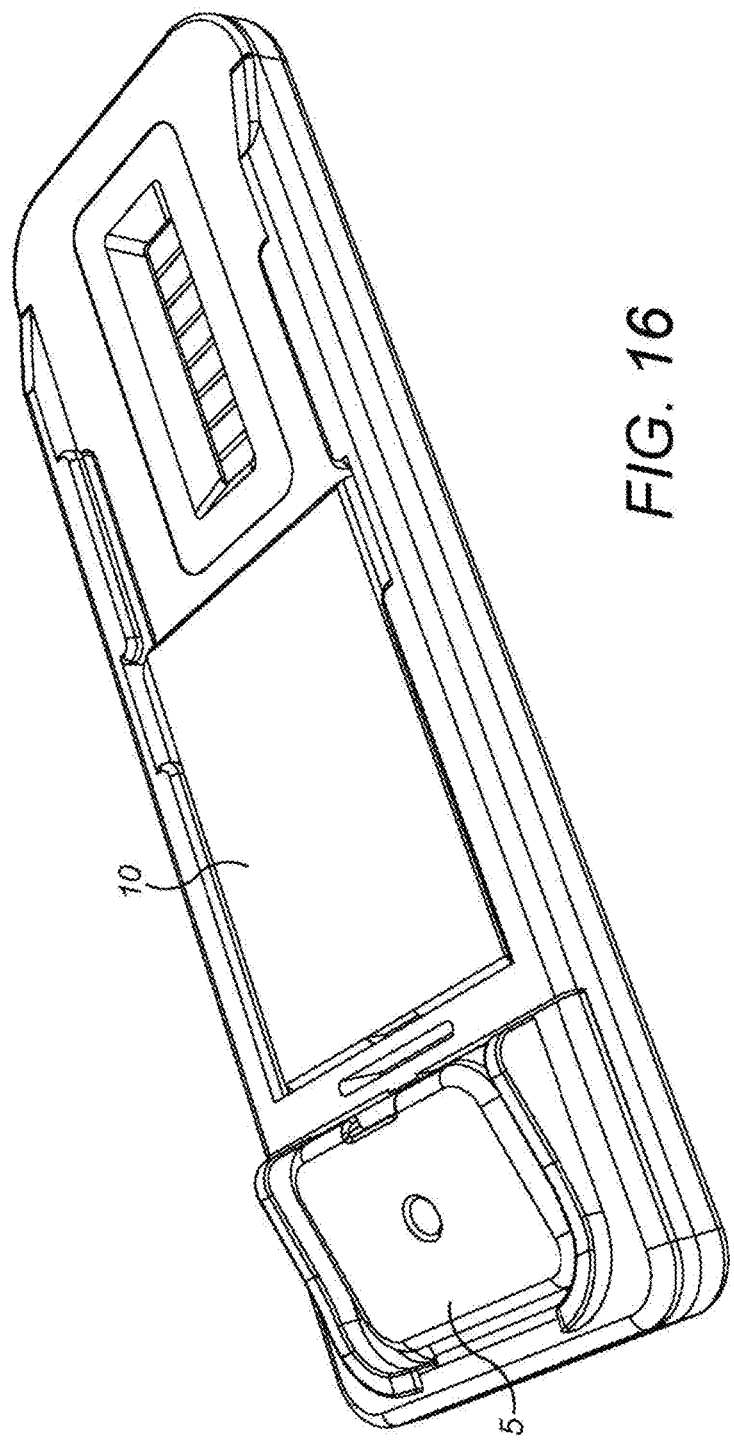
FIG. 16 shows the device of FIG. 1 with the shutter as it appears in both a first and a third configuration and with the solution capsule in an initial configuration.

The device 1 is supplied with the shutter 10 in the first position and the solution capsule 5 in the initial configuration (as shown in FIG. 16). The solution capsule 5 is supplied with a precise volume of a solution. This may be chosen to dissolve effectively one or more components of what would be expected to be present in a human finger print. It may, more specifically, be selected to dissolve effectively at least the chemical species of interest which the test is configured to detect.

When the device is to be used to perform a test, the shutter 10 is moved from the first position to the second position (as shown in FIG. 1). In doing this, the sample window 6 that bounds the skin-print receiving region 42 is revealed, having previously been hidden by the shutter. A user applies a skin-print (most likely a fingerprint) to the skin-print receiving region 42, perhaps under the guidance of another party.

Once the skin-print has been applied to the skin-print receiving region 42, the shutter 10 is moved from the second position to the third position (such that the device again appears the same as shown in FIG. 16). In the third position, the sample window 6 and the skin-print receiving region 42 are again hidden by the shutter 10. Instead, the result window 7 is revealed. Also, once the shutter is in the third position, the shutter cannot be moved back to the second position.

Figure 17:
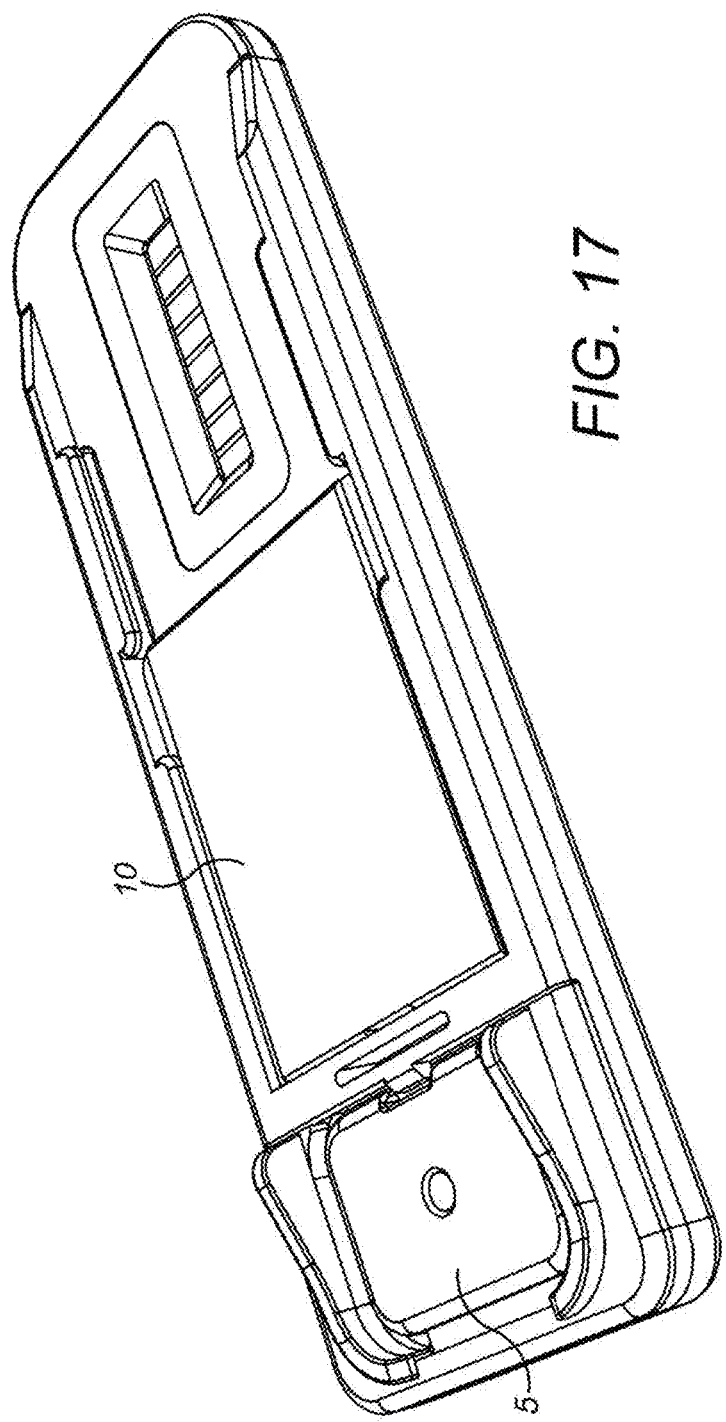
FIG. 17 shows the device of FIG. 1 with the shutter in a third configuration and the solution capsule in a subsequent configuration.

Subsequently, the user or another party applies a force to the planar base 53 of the solution capsule 5. If the force is above the threshold force (for example, 10 Newtons), the solution capsule 5 moves from its initial configuration, in which the solution is sealed within the solution capsule 5, into its subsequent configuration, in which the frangible enclosing member 54 is pierced by the pair of piercers 91, 92 to produce a pair of pierced holes in the frangible enclosing member. This is shown in FIG. 17.

As mentioned above, the distance between the piercers 91, 92 is configured such that, when the buffer capsule 5 enters the subsequent configuration, solution present in the buffer capsule 5 is drawn between the two piercers 91, 92. A surface tension present on the solution between the two piercers 91, 92 initiates a capillary pull action that draws a drop of solution out of the buffer capsule 5 to be absorbed by the solution-receiving region 43 of the substrate 4 that surrounds the pair of piercers 91, 92. Immediately after the drop of solution is released from between the two piercers 91, 92, there is an absence of solution between the two piercers which allows the opportunity for ambient air to enter the buffer capsule 5 in order to equalise pressure inside and outside the buffer capsule 5. Once the pressure is equalised, a further drop of solution is drawn between the two piercers 91, 92 and the same process is repeated. In this way, the release of solution onto the solution-receiving region 43 of the substrate 4 is controlled, albeit passively, at a constant rate.

The rate of flow of solution out of the solution capsule is influenced by, among other things, the width between the piercers 91, 92 and the viscosity of the solution being dispensed from the solution capsule 5. This is in part because the flow path is bounded by the two piercers 91, 92. In the first embodiment, the piercers are spaced apart a distance of 1 mm. In the event that the 300 µl of aqueous solution having the following properties: 10% methanol; 10 mM phosphate buffer; 0.05% Tween 80; pH7.4, is dispensed, it would be expected to exit the solution capsule at a constant rate over a period of approximately 1 to 2 minutes.

After leaving the solution capsule 5, solution is drawn down the substrate from the solution-receiving region 43 to the skin-print receiving region 42. Since the piercers are only separated by a 1 mm the location where the solution is deposited out of the solution capsule is precise. In this way, variation is reduced and results are more consistent. The widening of the substrate 4 with distance away from the source of the solution acts to draw the solution towards the skin-print receiving region 42 since the skin-print receiving region 42 has a greater capacity to absorb solution by virtue of being wider. The solution acts to dissolve chemical species that may be present in the skin-print off the skin-print receiving region 42. The solution, together with the dissolved chemical species, is drawn further down the substrate 4. Where the substrate becomes thinner, between the skin-print receiving region 42 and the analysis region 44, the solution becomes concentrated into a smaller area.

By configuring the solution capsule to dispense solution at approximately the rate described above, there is a relatively high efficiency in dissolving the chemicals species of an average-sized human fingerprint that has been deposited on the skin-print receiving region and carrying those chemicals species towards the analysis region 44.

If the analyte of interest is present in the skin-print (e.g. fingerprint) and is dissolved and carried with the solution to the analysis region 44, the analyte will bind with the labelled competitive binding assay that is present in the analysis region 44 downstream of the skin-print receiving region 42 but upstream of the result line 45. The labelled competitive binding assay is drawn further down the substrate 4 as the solution is drawn down.

If the labelled competitive binding assay has bound to the analyte (because the analyte is present), when the solution reaches the result line 45 its binding sites will be occupied and it will not bind to the protein-analyte conjugate that is immobilised on the result line 45. Hence, the labelled conjugate will pass through the result line (and the control line) towards the absorbent sink 47.

If, on the other hand, the labelled competitive binding assay has not bound to analyte (because the analyte is not present), when the solution reaches the result line 45 its binding sites will be available to bind with the protein-analyte conjugate that is immobilised on the result line 45. Hence, the labelled conjugate will become visible at the result line.

Whatever happens at the result line, a control assay (also labelled) that is present in the buffer solution will bind with an immobilised conjugate at the control line 46. Hence, the labelled control assay will become visible at the control line 46. This provides a user with confidence that the test has been successful, whether the result line 45 shows a positive or negative result.

Second Embodiment

Figure 19:
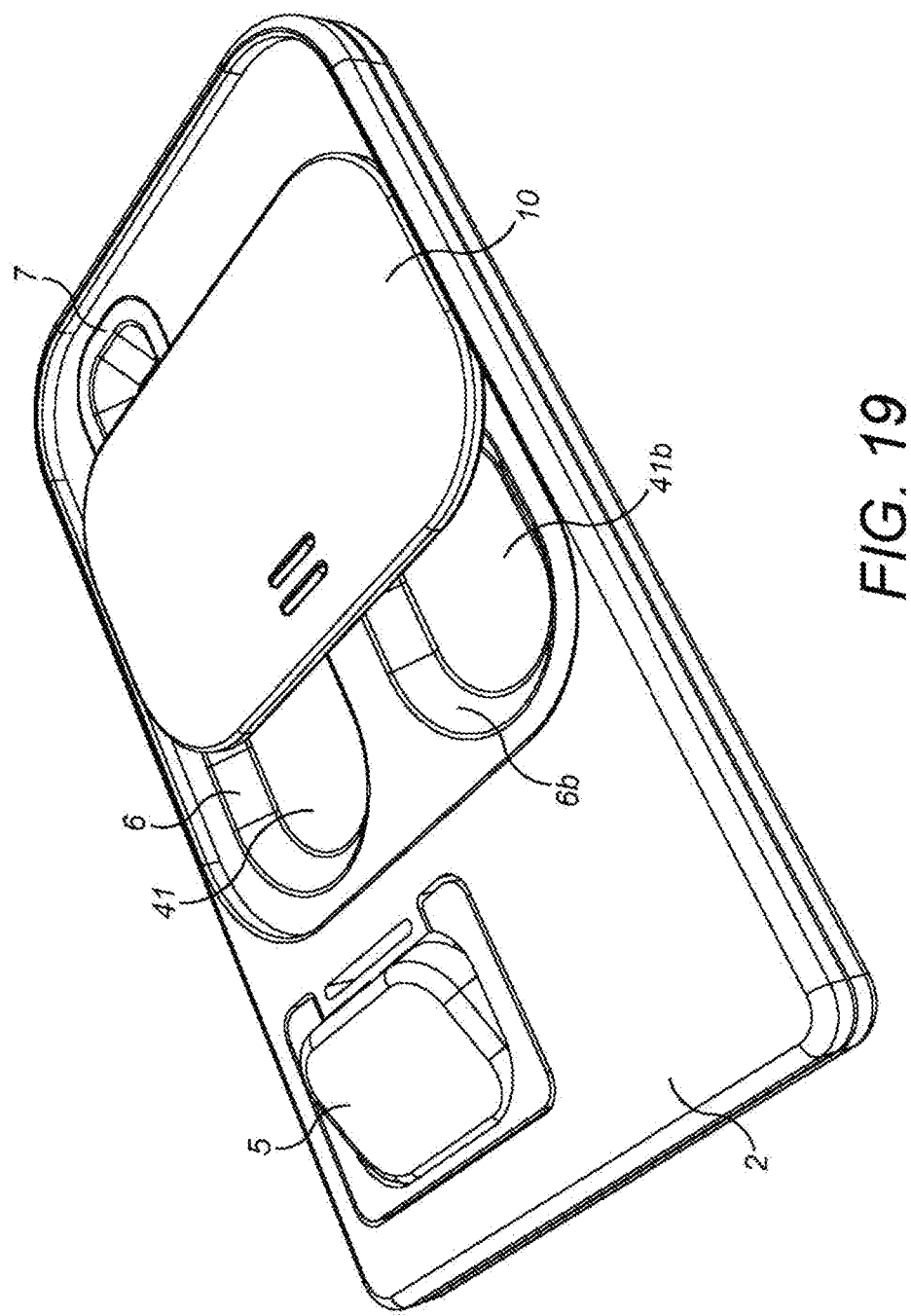
FIG. 19 shows a perspective view of a device in accordance with a second embodiment of the invention.

A second embodiment of the invention is illustrated in FIG. 19. This embodiment is largely similar to the first embodiment and also comprises a second skin-print receiving region 41b. The second skin-print receiving region 41b may be located on a second substrate that may be independent of the lateral flow substrate 4. For example, the second substrate may be of glass.

The second skin-print receiving region 41b may be bounded by a second sample window 6b adjacent the sample window 6. Unlike the first skin-print receiving region which, because of the lateral flow technique requires a wicking substrate, the second skin-print receiving region 41b may comprise a non-porous substrate.

Both sample windows 6, 6b and both skin-print receiving regions 41, 41b may be concealed by the shutter 10 in the first position of the shutter 10, revealed in the second position of the shutter 10 and concealed again by the shutter 10 in the third position of the shutter 10.

It may be the case that the second embodiment comprises further features that allow the shutter 10 to be released from the third position only on triggering of a tamper evident feature. Release from the third position in such circumstances may allow the shutter to move back to the second position, thus revealing the second sample window 6b and second skin-print receiving region 41b for a second time. This may allow an authorised user to analyse an image of the skin-print on the second skin-print receiving region 41b to confirm identity of the skin-print on the second skin-print receiving region 41b.

Other aspects of the second embodiment, where not explicitly described and/or illustrated as differing from the first embodiment, may be identical to those of the first embodiment.

Second Embodiment in Use

Use of the second embodiment is largely the same as that of the first embodiment, except that when the shutter is in the second position, a user is required not only to place a skin-print in the first skin-print receiving region 41 bounded by the sample window 6 but also to place a skin-print in the second skin-print receiving region 41b bounded by the second sample window 6b.

Further, analysis of the skin-print using the lateral flow technique may be conducted as per the first embodiment and, in addition, analysis as to the identity of the skin-print may be obtained separately by comparing the skin-print in the second skin-print receiving region 41b with, for example, a skin-print in a database.

Use of the second embodiment may involve a separate analysis of the second skin-print present in the second skin-print receiving region 41b. This separate analysis may involve triggering a tamper evident feature to release the shutter 10 from the third position. The separate analysis may comprise photographing the second skin-print in order to compare a photographed image with images in a database, for example. This analysis may take place at a different time and location from the lateral flow analysis, if required.

Third Embodiment

Figure 20:
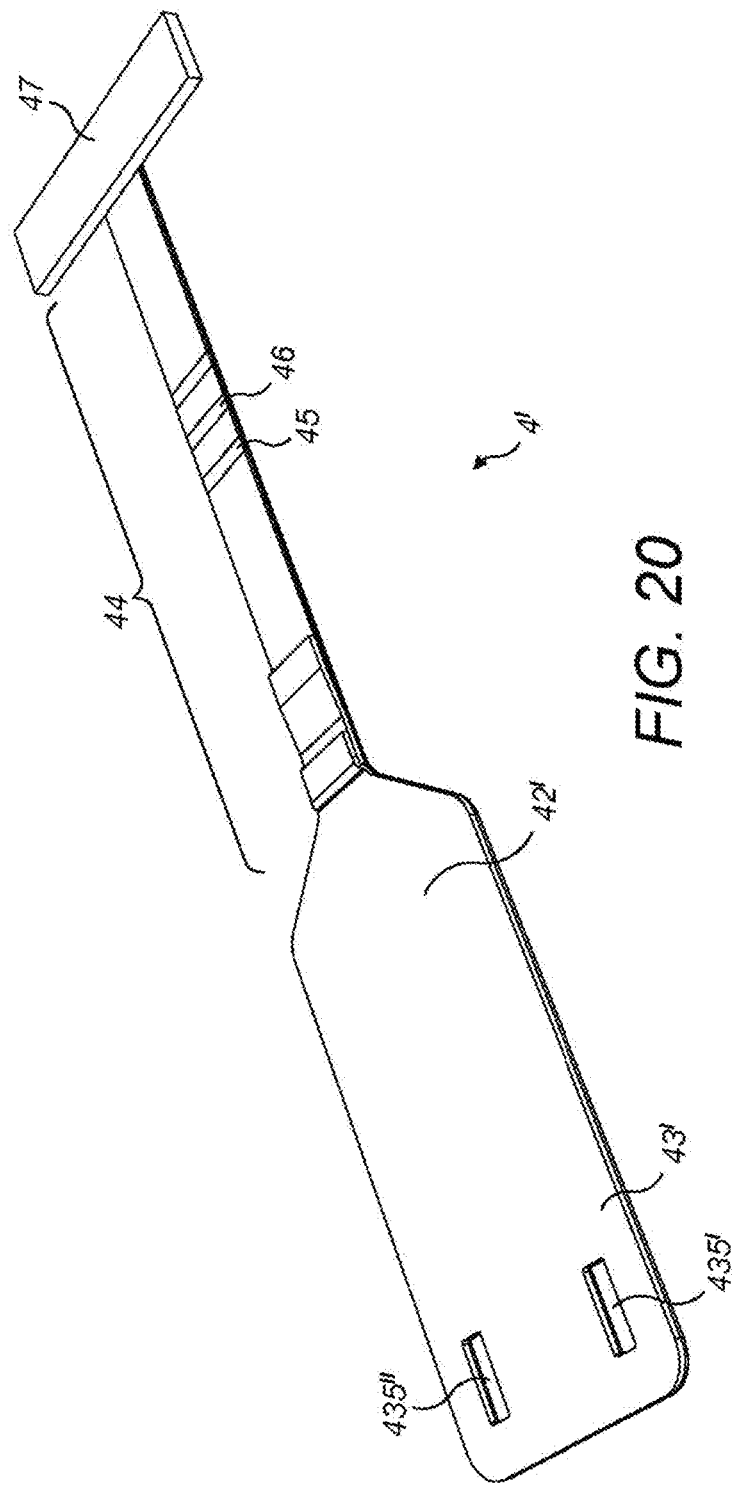
FIG. 20 shows a perspective view of a substrate in accordance with the third embodiment of the disclosure.
Figure 21:
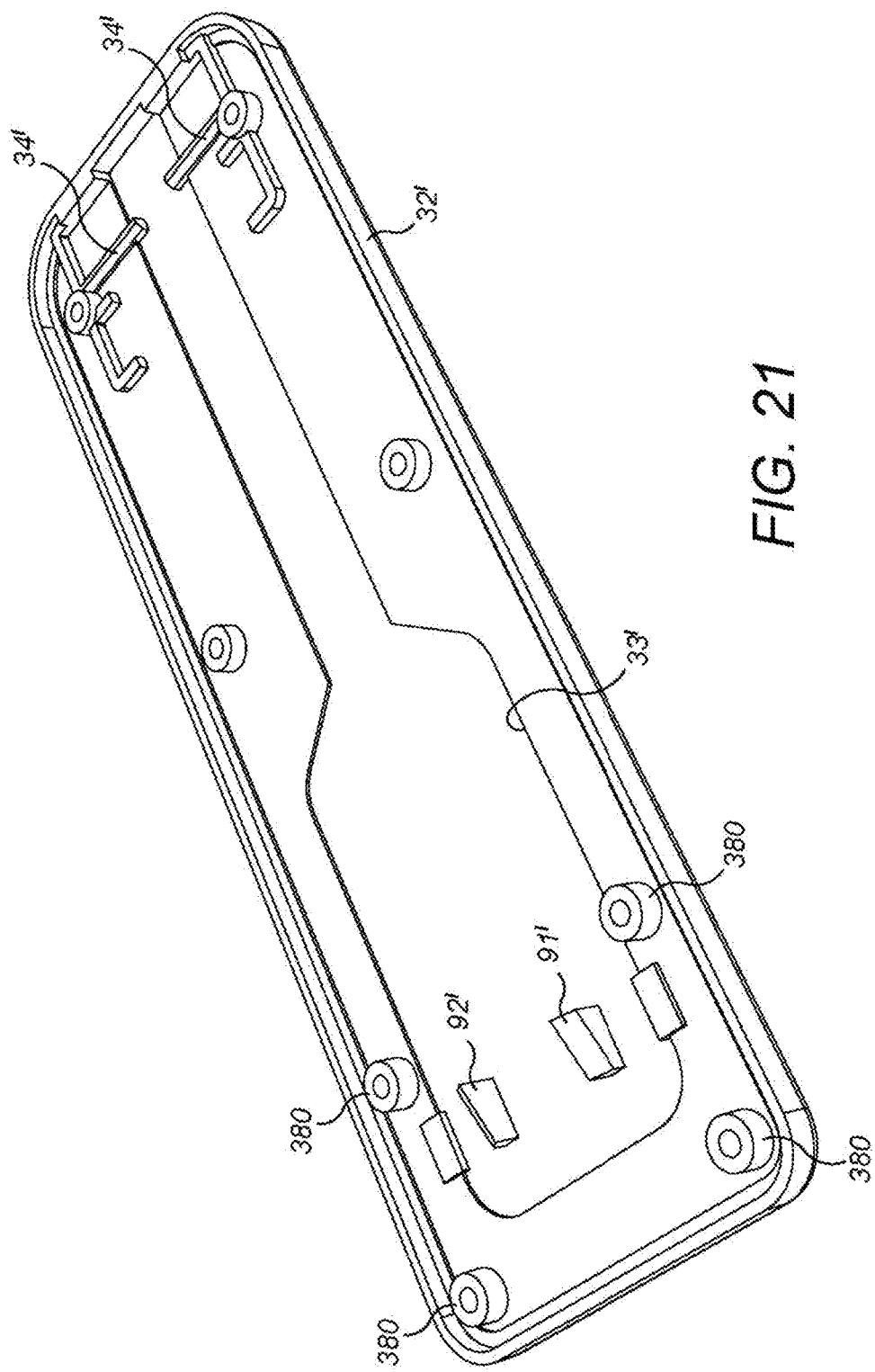
FIG. 21 shows a perspective view of a lower portion of the housing in accordance with a third embodiment of the disclosure.

FIG. 21 shows the lower portion 32' of the body 3 of the housing 2 of a third embodiment of the disclosure. A comparison of the lower portion 32' of the third embodiment may be made with the lower portion 32 of the first embodiment by comparing FIG. 21 with the lower-most component shown in FIG. 2. FIG. 20 shows a substrate 4' for use in the third embodiment. This compares with the substrate 4 of the first embodiment as illustrated in FIG. 4.

There are three main differences between the lower portion 32' of the third embodiment and the lower portion 32 of the first embodiment.

First, in the third embodiment, the spatial relationship of the piercers 91' 92' is different from that of the first embodiment. In particular, the piercers 91', 92' are spaced further apart in the third embodiment than are the piercers 91, 92 of the first embodiment. Preferably, the piercers are spaced apart by a distance of approximately 9 mm.

Secondly, the indentation 33' of the second embodiment has a different shape than that of the indentation 33 of the first embodiment. As in the first embodiment, the indentation 33' may reflect the shape of the substrate 4'. Accordingly, the substrate 4' (FIG. 20) of the third embodiment may have a different shape from the substrate 4 of the first embodiment.

Thirdly, the lower portion 32' of the third embodiment comprises locator components 34' that act to locate and/or retain the substrate 4 within the indentation 33' of the lower portion 32'.

Like the substrate 4 of the first embodiment, the substrate 4' of the third embodiment has a solution-receiving region 43' having a portion of constant width and a portion of narrowing width towards the analysis region 44. The analysis region 44 may be of constant width. The width of the absorbent sink 47 may again be wider.

Unlike the substrate 4 of the first embodiment, however, the solution receiving region 43' is, for most of its length, the same width as the portion of the skin-print receiving region 42 having a constant width. Rather than tapering towards an end furthest from the skin-print receiving region 42, instead, the end of the solution receiving region 43' furthest from the skin-print receiving region 42 has rounded corners.

The solution-receiving region 43' of the substrate 4' may comprise a pair of apertures 435', 435", one for each piercer 91', 92'.

Except where described otherwise, components of the third embodiment may be the same as those of the first embodiment.

Alternatives

The invention is not limited to particular aspects of either the first or the second embodiment. Many alternative aspects are considered to fall within the scope of the appended claims. The following is a non-exhaustive list of alternative aspects that fall within the scope of the claims.

The ability of the solution capsule 5 (and a mechanism by which solution is released) to release a specific volume of fluid at a specifically controlled rate may be achieved in a variety of different ways. In particular, the invention is not limited to the particular hinged rotating movement of the solution capsule 5 relative to the recess 60. For example, where there is a rotating action, it need be achieved by other means, such as a pivot. This may, for example, comprise an axle extending from opposite ends of the solution capsule 5.

Alternatively, it may be achieved by a pair of protrusions, one at each side of the solution capsule 5, and a pair of corresponding sockets in the recess 60 configured to receive the pair or protrusions and allow rotation thereof. In the illustrated embodiments, the pivoting arrangement is provided by a living hinge which thereby enables the capsule assembly 50 to be formed of a single moulded piece (excluding the frangible enclosing member 54).

Indeed, the invention is not limited to a rotational movement of the solution capsule 5. Instead, for example, movement of the solution capsule from the initial configuration to the subsequent configuration may be via a translational movement. For example, in a first translational position, an outlet from the solution capsule may align with a blocking member while, in a second translational position, an outlet from the solution capsule may align with a channel through which fluid may be drawn to the solution-receiving region 43 of the substrate 4. Such an arrangement may involve use of a slip latch or an alternative one-way, binary release mechanism.

Similarly, the slip-latch, where present, may be achieved by alternative means than that described in respect of the first embodiment.

Further, the invention is not limited to require a pair of piercing members. There may be a single piercing member, perhaps configured in such a manner as to produce more than one aperture in the frangible enclosing member 54. Alternatively, where present, a single piercing member may comprise a portion that may serve a purpose of drawing fluid in and, by virtue of a surface tension present on the solution within the portion, resulting in a capillary pull action that draws a drop of solution out of the buffer capsule 5 to be absorbed by the solution-receiving region 43 of the substrate 4.

Figure 15:
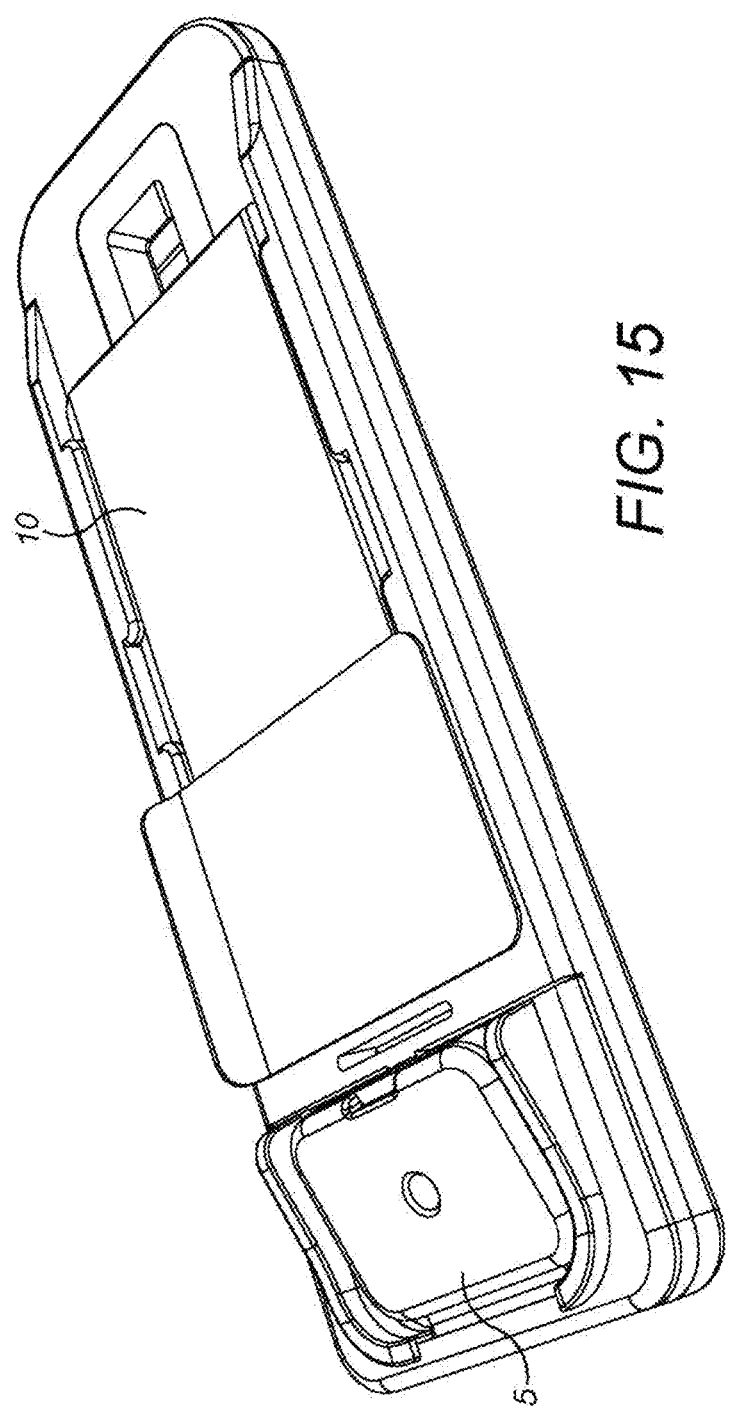
FIG. 15 shows a variation on the device of FIG. 1 having a tear-off strip in situ.

In addition, the technique by which the skin-print receiving region 43 of the substrate is protected prior to use may not be as discussed in relation to the first embodiment. For example, in the variation of the first embodiment and as shown in FIG. 15, the shutter 10 may have only two positions, corresponding to the second and third positions of the shutter 10 with reference to the first embodiment. Instead of the first shutter position, there may be a tear off strip to protect the skin-print receiving region 43 prior to use. In this way, the shutter 10 only needs the capability of moving once and only in one direction from the second position to the third position.

While the specific embodiments make use of passive control of rate of flow of fluid from the solution capsule 5 to the solution-receiving region 43, it is possible that active control might be employed. For example, there may be a constant fluid rate pump configured to actuate in a binary fashion and supply solution from the solution capsule 5 to the solution-receiving region 43 at a constant rate.

The hinged solution capsule and pair of piercers is one option for achieving a bistable release mechanism. Other options are possible and fall within the scope of the claim. The term "bistable release" is intended to require only two states: either fully on or fully off. In the same way that a domestic light switch is configured to have only two stable states (on or off), so the release mechanism of the present disclosure is intended to have only two conditions, both of which are stable. Application of a force of less than the threshold force results in the bistable release mechanism not being actuated while application of a force that is equal to or greater than the threshold force results in the bistable release mechanism being fully actuated. Partial actuation is not possible. That is not to say, however, that once the bistable release mechanism is actuated, all of the solution is dispensed instantaneously. On the contrary, in preferred embodiments of the invention, the release of solution from the capsule to the solution receiving region takes place over some tens or hundreds of seconds. The binary nature of the actuation, however, is such that, on actuation, the rate of flow is constant from the moment of actuation until the solution capsule is empty of solution and all of the solution is present on the substrate (assuming that the device is held in an appropriately level orientation).

In this way, by choosing an optimal flow rate, efficient use of the solution for the purposes of the lateral flow analysis can be maximised.

While the rate of flow of solution may be important in particular circumstances and while the quantum of fluid supplied in the solution capsule may be important in particular circumstances, the invention is of course not limited to a specific volume or rate of flow. The rate of flow and the volume of solution required may be related to factors including the area of the skin-print receiving region, the quantity of materials present on the substrate for the purpose of lateral flow analysis, and the desired sensitivity of the test, among other variables.

The detectable signal in the test site of the lateral flow device may be any form of detectable signal and is not limited to the examples given herein. The detectable signal may, for example, by a fluorescent marker.

A further alternative embodiment is a variation on the second embodiment illustrated in FIG. 19. The further embodiment may comprise two skin-print receiving regions wherein both skin-print receiving regions are configured for lateral flow analysis. In other words, there may be two lateral flow test strips in parallel. The device may be intended for two skin-prints to be applied, one to each skin-print receiving region, one immediately after another. It may be, however, that the analysis step for the two test strips is intended to be carried out at different times. For example, one may be actuated immediately after the skin-print has been applied while the other may be actuated at a later time.

Other alternatives and variations also fall within the scope of the appended claims.

The invention claimed is:

1. A lateral flow device for receiving and analysing a sample, wherein the analysing involves use of a solution, the device comprising:
 a substrate including a skin-print sample receiving portion for receiving a skin-print to be analysed, a solution-receiving region and an analysis region;
 a solution capsule connected to a body of the device by a hinge at a first end of the solution capsule, the solution capsule comprising a pierceable surface and containing a specific volume of solution, the solution capsule having a sealed configuration in which the solution capsule is sealed and a release configuration in which the specific volume of the solution contained in the solution capsule is released via a flow path that provides fluid communication between the solution capsule and the skin-print sample receiving portion; and
 a bistable release mechanism comprising a protrusion on the body that resists rotation of a second end of the solution capsule from a first stable orientation to a second stable orientation, the bistable release mechanism further comprising a piercing member configured to pierce the pierceable surface when the solution capsule is in the release configuration,
 wherein the bistable release mechanism releases only in the event that a force applied to the solution capsule reaches a threshold force sufficient to overcome a resistance from the protrusion and rotate the second end of the solution capsule from the first stable orientation to the second stable orientation, such that the piercing member projects through the pierceable surface of the solution capsule to form the flow path through which the specific volume of solution may flow in a drop-by-drop controlled release manner to the substrate resulting in one-way conversion of the solution capsule from the sealed configuration into the release configuration,
 wherein all of the specific volume of solution flows out of the solution capsule, is deposited on the solution-receiving region dropwise at a constant rate, is drawn to the skin-print sample receiving portion and on to the analysis region of the substrate to maximise efficiency of dissolving any chemical species of interest from the skin-print receiving region and carrying those chemical species towards the analysis region, and
 wherein substantially none of the specific volume of solution remains in the solution capsule at the conclusion of sample analysis.

2. The device of claim 1, the piercing member including a pair of piercers such that the piercing members initiate a capillary pull action that draws a drop of the solution out of the solution capsule to be absorbed by the solution-receiving region that surrounds the pair of piercers, and immediately after the drop of the solution is released from between the pair of piercers, there is an absence of solution between the two piercers which allows for ambient air to enter the solution capsule between the pair of piercers to equalise pressure inside and outside the solution capsule, wherein the release configuration of the solution capsule is configured to supply fluid to the flow path at a constant rate, wherein, for a particular solution, the rate is governed by:
 (a) a piercing area determined by each of the pair of piercers, in combination with
 (b) a dimension of a gap between each of the piercers of the pair of piercers.

3. The device of claim 1 further comprising the body comprising the sample receiving portion and wherein the one-way conversion of the solution capsule from the sealed configuration into the release configuration comprises movement of the solution capsule relative to the body.

4. The device of claim 1 wherein the solution capsule and the flow path are configured to passively enable a constant rate of flow.

5. The device of claim 1 further comprising the body, wherein the body comprises the piercing member and the solution capsule comprises the pierceable surface.

6. The device of claim 5 wherein the piercing member comprises a pair of piercers, wherein each piercer comprises a proximal end and a distal end, and wherein the distal end is more acutely shaped than the proximal end.

7. The device of claim 1 wherein the piercing member comprises a pair of piercers.

8. The device of claim 7 wherein, for a particular solution, the rate of flow is governed by:
 (a) a piercing area determined by each of the pair of piercers, in combination with
 (b) a dimension of a gap between each of the piercers of the pair of piercers.

9. The device of claim 7 wherein the pair of piercers are spaced apart such that a capillary pull action results which draws a drop of solution out of the solution capsule.

10. The device of claim 1 further comprising a further sample-receiving region for receiving a further sample to be analysed.

11. The device of claim 1 further comprising a housing that houses the sample receiving portion, the housing comprising at least a first part and a second part which are movable relative to one another
 i) from a first closed configuration in which the sample receiving portion is inaccessible;
 ii) to a first open configuration in which access to the sample receiving portion is enabled to allow capturing of a skin-print on the sample receiving portion; and subsequently
 iii) into a second closed configuration in which the sample receiving portion is again inaccessible.

12. The device of claim 1
 wherein the protrusion is located in a recess of the body of the device,
 wherein when the solution capsule is in the first configuration the first end of the solution capsule sits adjacent a first sidewall of the recess and the second end of the solution capsule sits substantially proud of a second sidewall of the recess,
 wherein the second end of the solution capsule is received in the recess in the second configuration.

13. A device for receiving and analysing a sample, wherein the analysing involves use of a solution, the device comprising:
 a substrate including a skin-print sample receiving portion for receiving a sample to be analysed;
 a body of the device in which the substrate is located, the body of the device having a window that is aligned with the skin-print sample receiving portion and configured to allow receipt of at least a part of an area of a skin-print on the skin-print sample receiving portion;

a solution capsule connected to the body of the device by a hinge at a first end of the solution capsule, the solution capsule containing a specific volume of solution, the solution capsule having a sealed configuration in which the solution capsule is sealed and a release configuration in which the specific volume of the solution contained in the solution capsule is released via a flow path that provides fluid communication between the solution capsule and the skin-print sample receiving portion; and a bistable release mechanism comprising a protrusion on the body that resists rotation of a second end of the solution capsule from a first stable orientation to a second stable orientation, wherein the bistable release mechanism releases only in the event that a force applied to the solution capsule reaches a threshold force sufficient to overcome a resistance from the protrusion and rotate the second end of the solution capsule from the first stable orientation to the second stable orientation, and wherein an application of the threshold force on the solution capsule results in one-way conversion of the solution capsule from the sealed configuration into the release configuration, such that all of the specific volume of solution flows out of the solution capsule and is deposited on the skin-print sample receiving portion of the substrate and none of the specific volume of solution remains in the solution capsule at the conclusion of a test, wherein the bistable release mechanism further comprises a piercing member comprising a pair of piercers and a pierceable surface configured to be pierced by the piercing member in the event of an application of the threshold force on the solution capsule, and wherein the flow path is bounded by the pair of piercers.

14. A device for receiving and analysing a skin-print sample, wherein the analysing involves use of a solution, the device comprising:

a substrate including a first skin-print sample receiving portion comprising a wicking material for receiving a skin-print sample to be analysed using the solution;

a second sample receiving portion comprising a non-porous substrate for receiving a skin-print sample for optical analysis;

a solution capsule connected to a body of the device by a hinge at a first end of the solution capsule, the solution capsule having a sealed configuration in which the solution capsule is sealed and a release configuration in which contents of the solution capsule are released via a flow path that provides fluid communication between the solution capsule and the first sample receiving portion; and a bistable release mechanism comprising a protrusion on the body of the device that resists rotation of a second end of the solution capsule from a first stable orientation to a second stable orientation, wherein the bistable release mechanism actuates only in the event that a force applied to the solution capsule reaches a threshold force sufficient to overcome a resistance from the protrusion and rotate the second end of the solution capsule from the first stable orientation to the second stable orientation, resulting in one-way conversion of the solution capsule from the sealed configuration into the release configuration, such that all of the specific volume of solution is released, wherein the bistable release mechanism further comprises a piercing member and a pierceable surface configured to be pierced by the piercing member when the solution capsule is in the release configuration such that the piercing member projects through the pierceable surface of the solution capsule to form an exit hole in the pierceable surface through which the solution may flow in a drop-by-drop controlled release manner to the substrate.

* * * * *